United States Patent [19]

Andree et al.

[11] Patent Number: 5,759,957
[45] Date of Patent: Jun. 2, 1998

[54] N-CYANOARYL NITROGEN HETEROCYCLES

[75] Inventors: Roland Andree; Mark Wilhelm Drewes, both of Langenfeld; Hans-Joachim Santel; Markus Dollinger, both of Leverkusen; Christoph Erdelen, Leichlingen, all of Germany

[73] Assignee: Bayer Aktiengesellschaft, Leverkusen, Germany

[21] Appl. No.: 581,537

[22] Filed: Jul. 8, 1996

[30] Foreign Application Priority Data

Apr. 25, 1994 [DE] Germany .................. 44 14 326.5
Oct. 19, 1994 [DE] Germany .................. 44 37 295.7

[51] Int. Cl.$^6$ ................. A01N 43/54; C07D 239/02
[52] U.S. Cl. .................. 504/243; 514/274; 544/309; 544/311; 544/312
[58] Field of Search ............. 544/309, 311, 544/313, 314, 245, 283, 284, 285, 295, 296, 310, 312; 504/136, 243; 514/274, 258, 259

[56] References Cited

U.S. PATENT DOCUMENTS

| | | | |
|---|---|---|---|
| 5,084,084 | 1/1992 | Satow et al. | 71/92 |
| 5,116,404 | 5/1992 | Ishii et al. | 544/309 |
| 5,127,935 | 7/1992 | Satow et al. | 544/309 |
| 5,154,755 | 10/1992 | Satow et al. | 544/310 |
| 5,356,863 | 10/1994 | Satow et al. | 504/243 |
| 5,416,236 | 5/1995 | Kawamura et al. | 564/99 |

*Primary Examiner*—John M. Ford
*Assistant Examiner*—Pavanram K. Sripada
*Attorney, Agent, or Firm*—Sprung Kramer Schaefer & Briscoe

[57] ABSTRACT

The invention relates to novel N-cyanoaryl nitrogen heterocycles of general formula

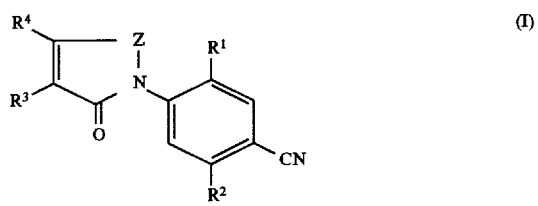

in which $R^1$, $R^2$, $R^3$, $R^4$ and Z have the meanings given in the description, several processes for producing them, their use as herbicides and insecticides and novel intermediate products.

23 Claims, No Drawings

N-CYANOARYL NITROGEN HETEROCYCLES

The invention relates to new N-cyanoaryl nitrogen heterocycles, to a plurality of processes for their preparation, to their use as herbicides and insecticides, and to new intermediates.

It has already been disclosed that certain N-cyanoaryl nitrogen heterocycles have herbicidal properties (cf. WO 91/00278, WO 92/11244, DE 4237920, EP 408382/U.S. Pat. No. 5,084,084, EP 438209, EP 473551). However, the herbicidal action, and the tolerance of the prior-art N-cyanoaryl nitrogen heterocycles with regard to crop plants, are not entirely satisfactory.

There have now been found the new N-cyanoaryl nitrogen heterocycles of the general formula (I)

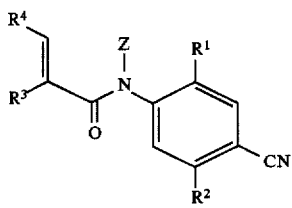

in which $R^1$ represents hydrogen or halogen,
$R^2$ represents the following group,

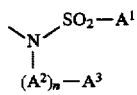

where n represents the numbers 0 or 1,
$A^1$ represents in each case optionally substituted alkyl, alkenyl, alkinyl, cycloalkyl, cycloalkylalkyl, aryl, arylalkyl, heterocyclyl or heterocyclylalkyl,
$A^2$ represents alkanediyl(alkylene) and
$A^3$ represents formyl, or represents in each case optionally substituted alkylcarbonyl, alkoxycarbonyl, alkylsulphonyl, cycloalkylcarbonyl, cycloalkylalkylcarbonyl, cycloalkylsulphonyl, cycloalkylalkylsulphonyl, arylcarbonyl, arylalkylcarbonyl, aryloxycarbonyl, arylsulphonyl, heterocyclylsulphonyl or heterocyclylalkylsulphonyl,
$R^3$ represents hydrogen, halogen, cyano or optionally substituted alkyl,
$R^4$ represents optionally substituted alkyl or together with $R^3$ represents alkanediyl,
Z represents one of the following groups

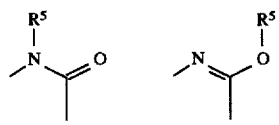

where $R^5$ represents hydrogen or in each case optionally substituted alkyl, alkenyl, alkinyl, alkylcarbonyl or alkoxycarbonyl, or represents amino or hydroxyl (in each case only bonded to N).

The general formula (I) thus represents the isomeric compounds of the general formulae (IA) and (IB) below

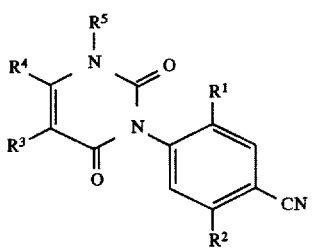

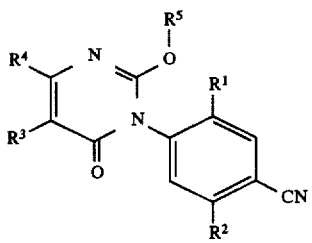

The new N-cyanoaryl nitrogen heterocycles of the general formula (I) are obtained when (a) to prepare compounds of the formula (IA) and (IB) in which $R^5$ represents hydrogen and $R^1$, $R^2$, $R^3$ and $R^4$ have the abovementioned meanings,
aminoalkenoic esters of the general formula (II)

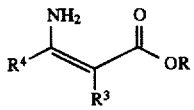

in which $R^3$ and $R^4$ have the abovementioned meanings and
R represents alkyl, aryl or arylalkyl,
are reacted with cyanoaryl isocyanates of the general formula (III)

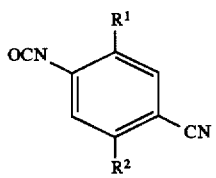

in which $R^1$ and $R^2$ have the abovementioned meanings,
or with cyanoarylurethanes(cyanoarylcarbamates) of the general formula (IV)

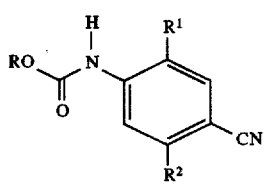

in which $R^1$ and $R^2$ have the abovementioned meanings and
R represents alkyl, aryl or arylalkyl,
if appropriate in the presence of a reaction auxiliary and if appropriate in the presence of a diluent, or when (b) to prepare compounds of the formulae (IA) and/or (IB) in which $R^5$ represents in each case optionally substituted alkyl, alkenyl, alkinyl, alkylcarbonyl or alkoxycarbonyl and $R^1$, $R^2$, $R^3$ and $R^4$ have the abovementioned meanings, N-cyanoaryl nitrogen heterocycles of the general formulae (IA) and/or (IB)
in which $R^5$ represents hydrogen and $R^1$, $R^2$, $R^3$ and $R^4$ have the abovementioned meanings,
are reacted with alkylating agents or acylating agents of the general formulae (V) or (VI)

$$X^1-R^5 \qquad (V)$$

$$R^5-O-SO_2-O-R^5 \qquad (VI)$$

in which
$R^5$ represents in each case optionally substituted alkyl, alkenyl, alkinyl, alkylcarbonyl or alkoxycarbonyl and
$X^1$ in formula (V) represents halogen,
if appropriate in the presence of an acid acceptor and if appropriate in the presence of a diluent,
or when
(c) to prepare compounds of the formula (I) in which $R^2$ represents the following group

and n, $A^1$, $A^2$, $A^3$, $R^1$, $R^3$, $R^4$ and Z have the abovementioned meanings,
N-cyanoaryl nitrogen heterocycles of the general formula (I) in which $R^2$ represents the group —NH—$SO_2$—$A^1$ and $A^1$, $R^1$, $R^3$, $R^4$ and Z have the abovementioned meanings,
are reacted with halogen compounds of the general formula (VII)

$$X^2-(A^2)_n-A^3 \qquad (VII)$$

in which
n, $A^2$ and $A^3$ have the abovementioned meanings and
$X^2$ represents halogen,
if appropriate in the presence of an acid acceptor and if appropriate in the presence of a diluent,
or when
(d) to prepare compounds of the formula (IA) in which $R^5$ represents amino or hydroxyl and $R^1$, $R^2$, $R^3$ and $R^4$ have the abovementioned meanings,
N-cyanoaryl nitrogen heterocycles of the general formulae (IA) and/or (IB) in which $R^5$ represents hydrogen and $R^1$, $R^2$, $R^3$ and $R^4$ have the abovementioned meanings,
are reacted with electrophilic aminating or hydroxylating agents, if appropriate in the presence of an acid acceptor and if appropriate in the presence of a diluent.

The new N-cyanoaryl nitrogen heterocycles of the general formula (I) are distinguished by a powerful herbicidal activity.

In the definitions, the saturated or unsaturated hydrocarbon chains, such as alkyl, alkanediyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably relates to compounds of the formula (I) in which
$R^1$ represents hydrogen, fluorine, chlorine or bromine, $R^2$ represents the group below

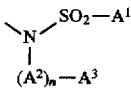

in which
n represents the numbers 0 or 1,
$A^1$ represents a radical from the series consisting of alkyl, alkenyl or alkinyl, each of which has up to 10 carbon atoms and each of which is optionally substituted by halogen, cyano or $C_1$–$C_4$-alkoxy,
$A^1$ furthermore represents cycloalkyl or cycloalkylalkyl having 3 to 8 carbon atoms in the cycloalkyl moiety and, if appropriate, 1 to 4 carbon atoms in the alkyl moiety, each of which is optionally substituted by halogen, cyano or $C_1$–$C_4$-alkyl,
$A^1$ furthermore represents aryl or arylalkyl having 6 or 10 carbon atoms in the aryl moiety and 1 to 4 carbon atoms in the alkyl moiety, each of which is optionally substituted by halogen, cyano, nitro, carboxyl, carbamoyl, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by fluorine and/or chlorine), by dimethylaminosulphonyl or diethylaminosulphonyl, by $C_1$–$C_4$-alkoxycarbonyl (which is optionally substituted by halogen, methoxy or ethoxy), by phenyl, phenyloxy or phenylthio (which are in each case optionally substituted by halogen, cyano, methyl, methoxy, trifluoromethyl and/or trifluoromethoxy),
$A^1$ furthermore represents heterocyclyl or heterocyclylalkyl having 2 to 6 carbon atoms and 1 to 4 nitrogen atoms and/or 1 to 2 oxygen or sulphur atoms in the saturated or unsaturated heterocyclyl moiety and, if appropriate, 1 to 4 carbon atoms in the alkyl moiety, each of which is optionally substituted by halogen, cyano, nitro, carboxyl, carbamoyl, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl or $C_1$–$C_4$-alkoxy-carbonyl (which are in each case optionally substituted by halogen), by phenyl, phenoxy or phenylthio (which are in each case optionally substituted by halogen, cyano, $C_1$–$C_4$-alkyl, $C_1$–$C_4$-halogenoalkyl, $C_1$14 $C_4$-alkoxy and/or $C_1$–$C_4$-halogenoalkoxy),
$A^2$ represents alkanediyl having 1 to 4 carbon atoms, and
$A^3$ represents formyl, or represents alkylcarbonyl, alkoxycarbonyl or alkylsulphonyl, each of which has up to 6 carbon atoms and each of which is optionally substituted by halogen or $C_1$–$C_4$-alkoxy, or represents cycloalkylcarbonyl, cycloalkylalkylcarbonyl, cycloalkylsulphonyl or cycloalkylalkylsulphonyl, each of which has 3 to 8 carbon atoms in the cycloalkyl moiety and, if appropriate, 1 to 4 carbon atoms in the alkyl moiety and each of which is optionally substituted by halogen, cyano or $C_1$–$C_4$-alkyl, or represents phenylcarbonyl, naphthylcarbonyl, phenylmethylcarbonyl, naphthylmethylcarbonyl, phenoxycarbonyl, naphthyloxycarbonyl, phenylsulphonyl, naphthylsulphonyl, phenylmethylsulphonyl, thienylsulphonyl, pyrazolyisulphonyl, pyridinylsulphonyl or pyridinylmethylsulphonyl (which are in each case optionally substituted by halogen, cyano, $C_1$–$C_4$-alkyl, $C_1$–$C_4$-alkoxy, $C_1$–$C_4$-halogenoalkyl, $C_1$–$C_4$-halogenoalkoxy or $C_1$–$C_4$-alkoxycarbonyl), R³ represents hydrogen, halogen, cyano, or alkyl having 1 to 6 carbon atoms which is substituted by halogen, R⁴ represents alkyl having 1 to 6 carbon atoms which is optionally substituted by halogen or $C_1$-$C_4$-alkoxy, or together with R³ represents alkanediyl having 2 to 8 carbon atoms, and Z represents one of the following groups

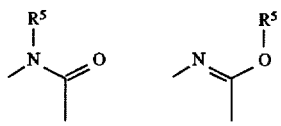

where

R⁵ represents hydrogen, or represents alkyl, alkenyl, alkinyl, alkylcarbonyl or alkoxycarbonyl, each of which has up to 6 carbon atoms and each of which is optionally substituted by fluorine, chlorine, bromine, cyano, $C_1$-$C_4$-alkoxy, $C_1$-$C_4$-alkyl-carbonyl or $C_1$-$C_4$-alkoxy-carbonyl, or represents amino or hydroxyl (in each case only bonded to N).

In particular, the invention relates to compounds of the formula (I) in which

R¹ represents hydrogen, fluorine or chlorine,

R² represents the group below

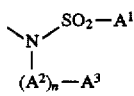

where n represents the numbers 0 or 1,

A¹ represents methyl, ethyl, n- or i-propyl, n-, i-, s- or t-butyl, n-, i-, s- or t-pentyl, each of which is optionally substituted by fluorine or chlorine, A¹ furthermore represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, methyl and/or ethyl, A¹ furthermore represents phenyl, naphthyl, phenylmethyl or phenylethyl, each of which is optionally substituted by fluorine, chlorine, bromine, cyano, nitro, carboxyl, methyl, trifluoromethyl, methoxy, ethoxy, difluoromethoxy, trifluoromethoxy, methylthio, ethylthio, methylsulphinyl, ethylsulphinyl, methylsulphonyl, ethylsulphonyl, dimethylaminosulphonyl, methoxycarbonyl, ethoxycarbonyl, propoxycarbonyl or phenyl, A¹ furthermore represents thienyl, pyrazolyl or pyridyl, each of which is optionally substituted by fluorine, chlorine, bromine, cyano, methyl, ethyl, trifluoromethyl, methoxy, ethoxy, methylthio, ethylthio, methylsulphinyl, ethylsulphinyl, methylsulphonyl, ethylsulphonyl, methoxycarbonyl or ethoxycarbonyl, A² represents methylene or dimethylene, and A³ represents formyl, or represents acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, each of which is optionally substituted by fluorine, chlorine, methoxy or ethoxy, or represents cyclopropylcarbonyl, cyclobutylcarbonyl, cyclopentylcarbonyl, cyclohexylcarbonyl, cyclopropylmethylcarbonyl, cyclobutylmethylcarbonyl, cyclopentylmethylcarbonyl, cyclohexylmethylcarbonyl, cyclopropylsulphonyl, cyclobutylsulphonyl, cyclopentylsulphonyl, cyclohexylsulphonyl, cyclopropylmethylsulphonyl, cyclobutylmethylsulphonyl, cyclopentylmethylsulphonyl or cyclohexylsulphonyl, each of which is optionally substituted by fluorine, chlorine, bromine, cyano, methyl or ethyl, or represents phenylcarbonyl, phenylmethylcarbonyl, phenoxycarbonyl, phenylsulphonyl, naphthylsulphonyl, phenylmethylsulphonyl, thienylsulphonyl or pyridinylsulphonyl (which are in each case optionally substituted by fluorine, chlorine, bromine, cyano, methyl, ethyl, methoxy, ethoxy, trifluoromethyl, difluoromethyl, difluoromethoxy, trifluoromethoxy, methoxycarbonyl or ethoxycarbonyl), R³ represents hydrogen, fluorine, chlorine, bromine, or represents methyl, ethyl, n- or i-propyl, each of which is optionally substituted by fluorine and/or chlorine, R⁴ represents methyl, ethyl, n- or i-propyl, each of which is optionally substituted by fluorine and/or chlorine, or together with R³ represents trimethylene or tetramethylene, and Z represents one of the groups below

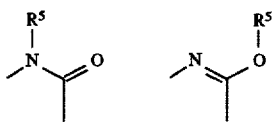

where

R⁵ represents hydrogen, or represents methyl, ethyl, n- or i-propyl, n-, i- or s-butyl, propenyl, butenyl, propinyl, butinyl, acetyl, propionyl, methoxycarbonyl or ethoxycarbonyl, each of which is optionally substituted by fluorine, chlorine or cyano, or represents amino or hydroxyl (in each case only bonded to N).

A very particularly preferred group of compounds of the formula (I) are the compounds of the formula (IA) in which R¹, R², R³, R⁴ and R⁵ have the meanings given above as being particularly preferred.

The abovementioned definitions of radicals, in general terms or in preferred ranges, apply to the end products of the formula (I) and also analogously to the starting materials and intermediates required in each case for the preparation.

These definitions of radicals can be combined with each other as desired, that is to say combinations between the abovementioned ranges of preferred compounds are also possible.

Examples of the compounds of the formula (I) or (IA) according to the invention are listed in Table 1 below.

TABLE 1

| Examples of the compounds of the formula (I) or (IA) | | | | |
|---|---|---|---|---|
| R¹ | R² | R³ | R⁴ | R⁵ |
| H | —N(SO₂CH₃)₂ | H | CF₃ | CH₃ |
| H | —N(SO₂CH₃)(SO₂C₂H₅) | H | CF₃ | CH₃ |
| H | —N(SO₂C₂H₅)₂ | H | CF₃ | CH₃ |
| H | —N(SO₂CH₃)(SO₂C₃H₇) | H | CF₃ | CH₃ |

TABLE 1-continued

Examples of the compounds of the formula (I) or (IA)

| R¹ | R² | R³ | R⁴ | R⁵ |
|---|---|---|---|---|
| H | —N(SO$_2$C$_3$H$_7$)$_2$ | H | CF$_3$ | CH$_3$ |
| H | —N(SO$_2$CH$_3$)(SO$_2$C$_3$H$_7$-i) | H | CF$_3$ | CH$_3$ |
| H | —N(SO$_2$C$_3$H$_7$-i)$_2$ | H | CF$_3$ | CH$_3$ |
| F | —N(SO$_2$CH$_3$)$_2$ | H | CF$_3$ | CH$_3$ |
| F | —N(SO$_2$CH$_3$)$_2$ | H | CF$_3$ | C$_2$H$_5$ |
| F | —N(SO$_2$CH$_3$)(SO$_2$C$_2$H$_5$) | H | CF$_3$ | CH$_3$ |
| F | —N(SO$_2$C$_2$H$_5$)$_2$ | H | CF$_3$ | CH$_3$ |
| F | —N(SO$_2$CH$_3$)(SO$_2$C$_3$H$_7$) | H | CF$_3$ | CH$_3$ |
| F | —N(SO$_2$C$_3$H$_7$)$_2$ | H | CF$_3$ | CH$_3$ |
| F | —N(SO$_2$CH$_3$)(SO$_2$C$_3$H$_7$-i) | H | CF$_3$ | CH$_3$ |
| F | —N(SO$_2$C$_3$H$_7$-i)$_2$ | H | CF$_3$ | CH$_3$ |
| F | —N(SO$_2$C$_2$H$_5$)(SO$_2$C$_3$H$_7$) | H | CF$_3$ | CH$_3$ |
| F | —N(SO$_2$CH$_3$)(SO$_2$-cyclopropyl) | H | CF$_3$ | CH$_3$ |
| F | —N(SO$_2$-cyclopropyl)$_2$ | H | CF$_3$ | CH$_3$ |
| F | —N(SO$_2$CH$_3$)(SO$_2$C$_4$H$_9$) | H | CF$_3$ | CH$_3$ |
| F | —N(SO$_2$C$_4$H$_9$)$_2$ | H | CF$_3$ | CH$_3$ |
| F | —N(SO$_2$CH$_3$)(SO$_2$CF$_3$) | H | CF$_3$ | CH$_3$ |
| F | —N(SO$_2$CF$_3$)$_2$ | H | CF$_3$ | CH$_3$ |
| F | —N(SO$_2$CH$_3$)(SO$_2$CH$_2$CF$_3$) | H | CF$_3$ | CH$_3$ |
| F | —N(SO$_2$CH$_2$CF$_3$)$_2$ | H | CF$_3$ | CH$_3$ |
| F | —N(SO$_2$CH$_3$)(SO$_2$C$_3$H$_6$Cl) | H | CF$_3$ | CH$_3$ |
| F | —N(SO$_2$CH$_2$CH$_2$CH$_2$Cl)$_2$ | H | CF$_3$ | CH$_3$ |
| F | —N(SO$_2$CH$_3$)(SO$_2$C$_6$H$_5$) | H | CF$_3$ | CH$_3$ |
| F | —N(SO$_2$C$_6$H$_5$)$_2$ | H | CF$_3$ | CH$_3$ |
| F | —N(SO$_2$C$_2$H$_5$)(SO$_2$C$_6$H$_5$) | H | CF$_3$ | CH$_3$ |
| F | —N(SO$_2$CH$_3$)(SO$_2$CH$_2$CH=CHCH$_3$) | H | CF$_3$ | CH$_3$ |
| F | —N(SO$_2$CH$_3$)$_2$ | H | CHF$_2$ | CH$_3$ |
| F | —N(SO$_2$CH$_3$)$_2$ | H | CHF$_2$ | C$_2$H$_5$ |
| F | —N(SO$_2$CH$_3$)(SO$_2$C$_2$H$_5$) | H | CHF$_2$ | CH$_3$ |
| F | —N(SO$_2$C$_2$H$_5$)$_2$ | H | CHF$_2$ | CH$_3$ |
| F | —N(SO$_2$CH$_3$)(SO$_2$C$_3$H$_7$) | H | CHF$_2$ | CH$_3$ |
| F | —N(SO$_2$C$_3$H$_7$)$_2$ | H | CHF$_2$ | CH$_3$ |
| F | —N(SO$_2$CH$_3$)(SO$_2$C$_3$H$_7$-i) | H | CHF$_2$ | CH$_3$ |
| F | —N(SO$_2$C$_3$H$_7$-i)$_2$ | H | CHF$_2$ | CH$_3$ |
| F | —N(SO$_2$C$_2$H$_5$)(SO$_2$C$_3$H$_7$) | H | CHF$_2$ | CH$_3$ |
| F | —N(SO$_2$CH$_3$)(SO$_2$-cyclopropyl) | H | CHF$_2$ | CH$_3$ |
| F | —N(SO$_2$-cyclopropyl)$_2$ | H | CHF$_2$ | CH$_3$ |
| F | —N(SO$_2$CH$_3$)(SO$_2$C$_4$H$_9$) | H | CHF$_2$ | CH$_3$ |
| F | —N(SO$_2$C$_4$H$_9$)$_2$ | H | CHF$_2$ | CH$_3$ |
| F | —N(SO$_2$CH$_3$)(SO$_2$CF$_3$) | H | CHF$_2$ | CH$_3$ |
| F | —N(SO$_2$CF$_3$)$_2$ | H | CHF$_2$ | CH$_3$ |
| F | —N(SO$_2$CH$_3$)(SO$_2$CH$_2$CF$_3$) | H | CHF$_2$ | CH$_3$ |
| F | —N(SO$_2$CH$_2$CF$_3$)$_2$ | H | CHF$_2$ | CH$_3$ |
| F | —N(SO$_2$CH$_3$)(SO$_2$C$_3$H$_6$Cl) | H | CHF$_2$ | CH$_3$ |
| F | —N(SO$_2$CH$_2$CH$_2$CH$_2$Cl)$_2$ | H | CHF$_2$ | CH$_3$ |
| F | —N(SO$_2$CH$_3$)(SO$_2$C$_6$H$_5$) | H | CHF$_2$ | CH$_3$ |
| F | —N(SO$_2$C$_6$H$_5$)$_2$ | H | CHF$_2$ | CH$_3$ |
| F | —N(SO$_2$C$_2$H$_5$)(SO$_2$C$_6$H$_5$) | H | CHF$_2$ | CH$_3$ |
| F | —N(SO$_2$CH$_3$)(SO$_2$CH$_2$CH=CHCH$_3$) | H | CHF$_2$ | CH$_3$ |
| F | —N(SO$_2$CH$_3$)$_2$ | H | CF$_2$Cl | CH$_3$ |
| F | —N(SO$_2$CH$_3$)$_2$ | H | CF$_2$Cl | C$_2$H$_5$ |
| F | —N(SO$_2$CH$_3$)(SO$_2$C$_2$H$_5$) | H | CF$_2$Cl | CH$_3$ |
| F | —N(SO$_2$C$_2$H$_5$)$_2$ | H | CF$_2$Cl | CH$_3$ |
| F | —N(SO$_2$CH$_3$)(SO$_2$C$_3$H$_7$) | H | CF$_2$Cl | CH$_3$ |
| F | —N(SO$_2$C$_3$H$_7$)$_2$ | H | CF$_2$Cl | CH$_3$ |
| F | —N(SO$_2$CH$_3$)(SO$_2$C$_3$H$_7$-i) | H | CF$_2$Cl | CH$_3$ |
| F | —N(SO$_2$C$_3$H$_7$-i)$_2$ | H | CF$_2$Cl | CH$_3$ |
| F | —N(SO$_2$C$_2$H$_5$)(SO$_2$C$_3$H$_7$) | H | CF$_2$Cl | CH$_3$ |
| F | —N(SO$_2$CH$_3$)(SO$_2$-cyclopropyl) | H | CF$_2$Cl | CH$_3$ |
| F | —N(SO$_2$-cyclopropyl)$_2$ | H | CF$_2$Cl | CH$_3$ |
| F | —N(SO$_2$CH$_3$)(SO$_2$C$_4$H$_9$) | H | CF$_2$Cl | CH$_3$ |
| F | —N(SO$_2$C$_4$H$_9$)$_2$ | H | CF$_2$Cl | CH$_3$ |
| F | —N(SO$_2$CH$_3$)(SO$_2$CF$_3$) | H | CF$_2$Cl | CH$_3$ |
| F | —N(SO$_2$CF$_3$)$_2$ | H | CF$_2$Cl | CH$_3$ |
| F | —N(SO$_2$CH$_3$)(SO$_2$CH$_2$CF$_3$) | H | CF$_2$Cl | CH$_3$ |
| F | —N(SO$_2$CH$_2$CF$_3$)$_2$ | H | CF$_2$Cl | CH$_3$ |
| F | —N(SO$_2$CH$_3$)(SO$_2$C$_3$H$_6$Cl) | H | CF$_2$Cl | CH$_3$ |
| F | —N(SO$_2$CH$_2$CH$_2$CH$_2$Cl)$_2$ | H | CF$_2$Cl | CH$_3$ |
| F | —N(SO$_2$CH$_3$)(SO$_2$C$_6$H$_5$) | H | CF$_2$Cl | CH$_3$ |
| F | —N(SO$_2$C$_6$H$_5$)$_2$ | H | CF$_2$Cl | CH$_3$ |
| F | —N(SO$_2$C$_2$H$_5$)(SO$_2$C$_6$H$_5$) | H | CF$_2$Cl | CH$_3$ |
| F | —N(SO$_2$CH$_3$)(SO$_2$CH$_2$CH=CHCH$_3$) | H | CF$_2$Cl | CH$_3$ |
| F | —N(SO$_2$CH$_3$)$_2$ | H | C$_2$F$_5$ | CH$_3$ |
| F | —N(SO$_2$CH$_3$)$_2$ | H | C$_2$F$_5$ | C$_2$H$_5$ |
| F | —N(SO$_2$CH$_3$)(SO$_2$C$_2$H$_5$) | H | C$_2$F$_5$ | CH$_3$ |
| F | —N(SO$_2$C$_2$H$_5$)$_2$ | H | C$_2$F$_5$ | CH$_3$ |
| F | —N(SO$_2$CH$_3$)(SO$_2$C$_3$H$_7$) | H | C$_2$F$_5$ | CH$_3$ |
| F | —N(SO$_2$C$_3$H$_7$)$_2$ | H | C$_2$F$_5$ | CH$_3$ |
| F | —N(SO$_2$CH$_3$)(SO$_2$C$_3$H$_7$-i) | H | C$_2$F$_5$ | CH$_3$ |
| F | —N(SO$_2$C$_3$H$_7$-i)$_2$ | H | C$_2$F$_5$ | CH$_3$ |
| F | —N(SO$_2$C$_2$H$_5$)(SO$_2$C$_3$H$_7$) | H | C$_2$F$_5$ | CH$_3$ |
| F | —N(SO$_2$CH$_3$)(SO$_2$-cyclopropyl) | H | C$_2$F$_5$ | CH$_3$ |
| F | —N(SO$_2$-cyclopropyl)$_2$ | H | C$_2$F$_5$ | CH$_3$ |
| F | —N(SO$_2$CH$_3$)(SO$_2$C$_4$H$_9$) | H | C$_2$F$_5$ | CH$_3$ |
| F | —N(SO$_2$C$_4$H$_9$)$_2$ | H | C$_2$F$_5$ | CH$_3$ |
| F | —N(SO$_2$CH$_3$)(SO$_2$CF$_3$) | H | C$_2$F$_5$ | CH$_3$ |
| F | —N(SO$_2$CF$_3$)$_2$ | H | C$_2$F$_5$ | CH$_3$ |

TABLE 1-continued

Examples of the compounds of the formula (I) or (IA)

| R¹ | R² | R³ | R⁴ | R⁵ |
|---|---|---|---|---|
| F | —N(SO₂CH₃)(SO₂CH₂CF₃) | H | C₂F₅ | CH₃ |
| F | —N(SO₂CH₂CF₃)₂ | H | C₂F₅ | CH₃ |
| F | —N(SO₂CH₃)(SO₂C₃H₆Cl) | H | C₂F₅ | CH₃ |
| F | —N(SO₂CH₂CH₂CH₂Cl)₂ | H | C₂F₅ | CH₃ |
| F | —N(SO₂CH₃)(SO₂C₆H₅) | H | C₂F₅ | CH₃ |
| F | —N(SO₂C₆H₅)₂ | H | C₂F₅ | CH₃ |
| F | —N(SO₂C₂H₅)(SO₂C₆H₅) | H | C₂F₅ | CH₃ |
| F | 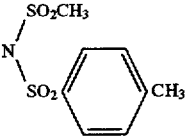 | H | C₂F₅ | CH₃ |
| F | —N(SO₂CH₃)₂ | CH₃ | CF₃ | CH₃ |
| F | —N(SO₂CH₃)₂ | CH₃ | CF₃ | C₂H₅ |
| F | —N(SO₂CH₃)(SO₂C₂H₅) | CH₃ | CF₃ | CH₃ |
| F | —N(SO₂C₂H₅)₂ | CH₃ | CF₃ | CH₃ |
| F | —N(SO₂CH₃)(SO₂C₃H₇) | CH₃ | CF₃ | CH₃ |
| F | —N(SO₂C₃H₇)₂ | CH₃ | CF₃ | CH₃ |
| F | —N(SO₂CH₃)(SO₂C₃H₇-i) | CH₃ | CF₃ | CH₃ |
| F | —N(SO₂C₃H₇-i)₂ | CH₃ | CF₃ | CH₃ |
| F | —N(SO₂C₂H₅)(SO₂C₃H₇) | CH₃ | CF₃ | CH₃ |
| F | 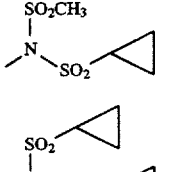 | CH₃ | CF₃ | CH₃ |
| F | 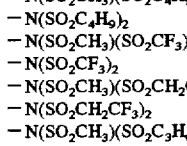 | CH₃ | CF₃ | CH₃ |
| F | —N(SO₂CH₃)(SO₂C₄H₉) | CH₃ | CF₃ | CH₃ |
| F | —N(SO₂C₄H₉)₂ | CH₃ | CF₃ | CH₃ |
| F | —N(SO₂CH₃)(SO₂CF₃) | CH₃ | CF₃ | CH₃ |
| F | —N(SO₂CF₃)₂ | CH₃ | CF₃ | CH₃ |
| F | —N(SO₂CH₃)(SO₂CH₂CF₃) | CH₃ | CF₃ | CH₃ |
| F | —N(SO₂CH₂CF₃)₂ | CH₃ | CF₃ | CH₃ |
| F | —N(SO₂CH₃)(SO₂C₃H₆Cl) | CH₃ | CF₃ | CH₃ |
| F | —N(SO₂CH₂CH₂CH₂Cl)₂ | CH₃ | CF₃ | CH₃ |
| F | —N(SO₂CH₃)(SO₂C₆H₅) | CH₃ | CF₃ | CH₃ |
| F | —N(SO₂C₆H₅)₂ | CH₃ | CF₃ | CH₃ |
| F | —N(SO₂C₂H₅)(SO₂C₆H₅) | CH₃ | CF₃ | CH₃ |
| F | 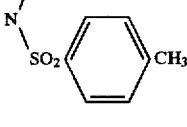 | CH₃ | CF₃ | CH₃ |
| F | —N(SO₂CH₃)₂ | Cl | CF₃ | CH₃ |
| F | —N(SO₂CH₃)₂ | Cl | CF₃ | C₂H₅ |
| F | —N(SO₂CH₃)(SO₂C₂H₅) | Cl | CF₃ | CH₃ |
| F | —N(SO₂C₂H₅)₂ | Cl | CF₃ | CH₃ |
| F | —N(SO₂CH₃)(SO₂C₃H₇) | Cl | CF₃ | CH₃ |
| F | —N(SO₂C₃H₇)₂ | Cl | CF₃ | CH₃ |
| F | —N(SO₂CH₃)(SO₂C₃H₇-i) | Cl | CF₃ | CH₃ |
| F | —N(SO₂C₃H₇-i)₂ | Cl | CF₃ | CH₃ |
| F | —N(SO₂C₂H₅)(SO₂C₃H₇) | Cl | CF₃ | CH₃ |
| F | 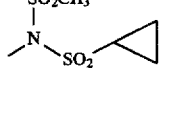 | Cl | CF₃ | CH₃ |
| F | 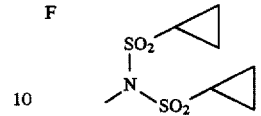 | Cl | CF₃ | CH₃ |
| F | —N(SO₂CH₃)(SO₂C₄H₉) | Cl | CF₃ | CH₃ |
| F | —N(SO₂C₄H₉)₂ | Cl | CF₃ | CH₃ |
| F | —N(SO₂CH₃)(SO₂CF₃) | Cl | CF₃ | CH₃ |
| F | —N(SO₂CF₃)₂ | Cl | CF₃ | CH₃ |
| F | —N(SO₂CH₃)(SO₂CH₂CF₃) | Cl | CF₃ | CH₃ |
| F | —N(SO₂CH₂CF₃)₂ | Cl | CF₃ | CH₃ |
| F | —N(SO₂CH₃)(SO₂C₃H₆Cl) | Cl | CF₃ | CH₃ |
| F | —N(SO₂CH₂CH₂CH₂Cl)₂ | Cl | CF₃ | CH₃ |
| F | —N(SO₂CH₃)(SO₂C₆H₅) | Cl | CF₃ | CH₃ |
| F | —N(SO₂C₆H₅)₂ | Cl | CF₃ | CH₃ |
| F | —N(SO₂C₂H₅)(SO₂C₆H₅) | Cl | CF₃ | CH₃ |
| F | 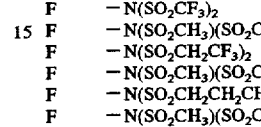 | Cl | CF₃ | CH₃ |
| F | —N(SO₂CH₃)₂ | CH₃ | CHF₂ | CH₃ |
| F | —N(SO₂CH₃)₂ | CH₃ | CHF₂ | C₂H₅ |
| F | —N(SO₂CH₃)(SO₂C₂H₅) | CH₃ | CHF₂ | CH₃ |
| F | —N(SO₂C₂H₅)₂ | CH₃ | CHF₂ | CH₃ |
| F | —N(SO₂CH₃)(SO₂C₃H₇) | CH₃ | CHF₂ | CH₃ |
| F | —N(SO₂C₃H₇)₂ | CH₃ | CHF₂ | CH₃ |
| F | —N(SO₂CH₃)(SO₂C₃H₇-i) | CH₃ | CHF₂ | CH₃ |
| F | —N(SO₂C₃H₇-i)₂ | CH₃ | CHF₂ | CH₃ |
| F | —N(SO₂C₂H₅)(SO₂C₃H₇) | CH₃ | CHF₂ | CH₃ |
| F | 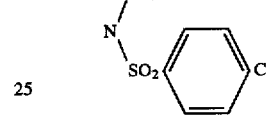 | CH₃ | CHF₂ | CH₃ |
| F | 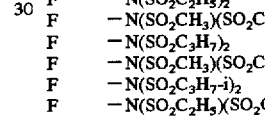 | CH₃ | CHF₂ | CH₃ |
| F | —N(SO₂CH₃)(SO₂C₄H₉) | CH₃ | CHF₂ | CH₃ |
| F | —N(SO₂C₄H₉)₂ | CH₃ | CHF₂ | CH₃ |
| F | —N(SO₂CH₃)(SO₂CF₃) | CH₃ | CHF₂ | CH₃ |
| F | —N(SO₂CF₃)₂ | CH₃ | CHF₂ | CH₃ |
| F | —N(SO₂CH₃)(SO₂CH₂CF₃) | CH₃ | CHF₂ | CH₃ |
| F | —N(SO₂CH₂CF₃)₂ | CH₃ | CHF₂ | CH₃ |
| F | —N(SO₂CH₃)(SO₂C₃H₆Cl) | CH₃ | CHF₂ | CH₃ |
| F | —N(SO₂CH₂CH₂CH₂Cl)₂ | CH₃ | CHF₂ | CH₃ |
| F | —N(SO₂CH₃)(SO₂C₆H₅) | CH₃ | CHF₂ | CH₃ |
| F | —N(SO₂C₆H₅)₂ | CH₃ | CHF₂ | CH₃ |
| F | —N(SO₂C₂H₅)(SO₂C₆H₅) | CH₃ | CHF₂ | CH₃ |
| F | 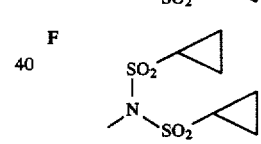 | CH₃ | CHF₂ | CH₃ |
| F | —N(SO₂CH₃)₂ | Cl | CHF₂ | CH₃ |
| F | —N(SO₂CH₃)₂ | Cl | CHF₂ | C₂H₅ |
| F | —N(SO₂CH₃)(SO₂C₂H₅) | Cl | CHF₂ | CH₃ |
| F | —N(SO₂C₂H₅)₂ | Cl | CHF₂ | CH₃ |
| F | —N(SO₂CH₃)(SO₂C₃H₇) | Cl | CHF₂ | CH₃ |
| F | —N(SO₂C₃H₇)₂ | Cl | CHF₂ | CH₃ |
| F | —N(SO₂CH₃)(SO₂C₃H₇-i) | Cl | CHF₂ | CH₃ |
| F | —N(SO₂C₃H₇-i)₂ | Cl | CHF₂ | CH₃ |
| F | —N(SO₂C₂H₅)(SO₂C₃H₇) | Cl | CHF₂ | CH₃ |

TABLE 1-continued

Examples of the compounds of the formula (I) or (IA)

| R¹ | R² | R³ | R⁴ | R⁵ |
|---|---|---|---|---|
| F | SO₂CH₃–N(CH₃)–SO₂-cyclopropyl | Cl | CHF₂ | CH₃ |
| F | SO₂-cyclopropyl–N(CH₃)–SO₂-cyclopropyl | Cl | CHF₂ | CH₃ |
| F | —N(SO₂CH₃)(SO₂C₄H₉) | Cl | CHF₂ | CH₃ |
| F | —N(SO₂C₄H₉)₂ | Cl | CHF₂ | CH₃ |
| F | —N(SO₂CH₃)(SO₂CF₃) | Cl | CHF₂ | CH₃ |
| F | —N(SO₂CF₃)₂ | Cl | CHF₂ | CH₃ |
| F | —N(SO₂CH₃)(SO₂CH₂CF₃) | Cl | CHF₂ | CH₃ |
| F | —N(SO₂CH₂CF₃)₂ | Cl | CHF₂ | CH₃ |
| F | —N(SO₂CH₃)(SO₂C₃H₆Cl) | Cl | CHF₂ | CH₃ |
| F | —N(SO₂CH₂CH₂CH₂Cl)₂ | Cl | CHF₂ | CH₃ |
| F | —N(SO₂CH₃)(SO₂C₆H₅) | Cl | CHF₂ | CH₃ |
| F | —N(SO₂C₆H₅)₂ | Cl | CHF₂ | CH₃ |
| F | —N(SO₂C₂H₅)(SO₂C₆H₅) | Cl | CHF₂ | CH₃ |
| F | SO₂CH₃–N(CH₃)–SO₂-(4-methylphenyl) | Cl | CHF₂ | CH₃ |
| H | —N(SO₂CH₃)₂ | H | CF₂Cl | CH₃ |
| H | —N(SO₂CH₃)₂ | H | CF₂Cl | C₂H₅ |
| H | —N(SO₂CH₃)(SO₂C₂H₅) | H | CF₂Cl | CH₃ |
| H | —N(SO₂C₂H₅)₂ | H | CF₂Cl | CH₃ |
| H | —N(SO₂CH₃)(SO₂C₃H₇) | H | CF₂Cl | CH₃ |
| H | —N(SO₂C₃H₇)₂ | H | CF₂Cl | CH₃ |
| H | —N(SO₂CH₃)(SO₂C₃H₇-i) | H | CF₂Cl | CH₃ |
| H | —N(SO₂C₃H₇-i)₂ | H | CF₂Cl | CH₃ |
| H | —N(SO₂C₂H₅)(SO₂C₃H₇) | H | CF₂Cl | CH₃ |
| H | SO₂CH₃–N(CH₃)–SO₂-cyclopropyl | H | CF₂Cl | CH₃ |
| H | SO₂-cyclopropyl–N(CH₃)–SO₂-cyclopropyl | H | CF₂Cl | CH₃ |
| H | —N(SO₂CH₃)(SO₂C₄H₉) | H | CF₂Cl | CH₃ |
| H | —N(SO₂C₄H₉)₂ | H | CF₂Cl | CH₃ |
| H | —N(SO₂CH₃)(SO₂CF₃) | H | CF₂Cl | CH₃ |
| H | —N(SO₂CF₃)₂ | H | CF₂Cl | CH₃ |
| H | —N(SO₂CH₃)(SO₂CH₂CF₃) | H | CF₂Cl | CH₃ |
| H | —N(SO₂CH₂CF₃)₂ | H | CF₂Cl | CH₃ |
| H | —N(SO₂CH₃)(SO₂C₃H₆Cl) | H | CF₂Cl | CH₃ |
| H | —N(SO₂CH₂CH₂CH₂Cl)₂ | H | CF₂Cl | CH₃ |
| H | —N(SO₂CH₃)(SO₂C₆H₅) | H | CF₂Cl | CH₃ |
| H | —N(SO₂C₆H₅)₂ | H | CF₂Cl | CH₃ |
| H | —N(SO₂C₂H₅)(SO₂C₆H₅) | H | CF₂Cl | CH₃ |
| H | SO₂CH₃–N(CH₃)–SO₂-(4-methylphenyl) | H | CF₂Cl | CH₃ |
| F | —N(SO₂CH₃)₂ | CH₃ | CF₂Cl | CH₃ |
| F | —N(SO₂CH₃)₂ | CH₃ | CF₂Cl | C₂H₅ |
| F | —N(SO₂CH₃)(SO₂C₂H₅) | CH₃ | CF₂Cl | CH₃ |
| F | —N(SO₂C₂H₅)₂ | CH₃ | CF₂Cl | CH₃ |
| F | —N(SO₂CH₃)(SO₂C₃H₇) | CH₃ | CF₂Cl | CH₃ |
| F | —N(SO₂C₃H₇)₂ | CH₃ | CF₂Cl | CH₃ |
| F | —N(SO₂CH₃)(SO₂C₃H₇-i) | CH₃ | CF₂Cl | CH₃ |
| F | —N(SO₂C₃H₇-i)₂ | CH₃ | CF₂Cl | CH₃ |
| F | —N(SO₂C₂H₅)(SO₂C₃H₇) | CH₃ | CF₂Cl | CH₃ |
| F | SO₂CH₃–N(CH₃)–SO₂-cyclopropyl | CH₃ | CF₂Cl | CH₃ |
| F | SO₂-cyclopropyl–N(CH₃)–SO₂-cyclopropyl | CH₃ | CF₂Cl | CH₃ |
| F | —N(SO₂CH₃)(SO₂C₄H₉) | CH₃ | CF₂Cl | CH₃ |
| F | —N(SO₂C₄H₉)₂ | CH₃ | CF₂Cl | CH₃ |
| F | —N(SO₂CH₃)(SO₂CF₃) | CH₃ | CF₂Cl | CH₃ |
| F | —N(SO₂CF₃)₂ | CH₃ | CF₂Cl | CH₃ |
| F | —N(SO₂CH₃)(SO₂CH₂CF₃) | CH₃ | CF₂Cl | CH₃ |
| F | —N(SO₂CH₂CF₃)₂ | CH₃ | CF₂Cl | CH₃ |
| F | —N(SO₂CH₃)(SO₂C₃H₆Cl) | CH₃ | CF₂Cl | CH₃ |
| F | —N(SO₂CH₂CH₂CH₂Cl)₂ | CH₃ | CF₂Cl | CH₃ |
| F | —N(SO₂CH₃)(SO₂C₆H₅) | CH₃ | CF₂Cl | CH₃ |
| F | —N(SO₂C₆H₅)₂ | CH₃ | CF₂Cl | CH₃ |
| F | —N(SO₂C₂H₅)(SO₂C₆H₅) | CH₃ | CF₂Cl | CH₃ |
| F | SO₂CH₃–N(CH₃)–SO₂-(4-methylphenyl) | CH₃ | CF₂Cl | CH₃ |
| F | —N(SO₂CH₃)₂ | Cl | CF₂Cl | CH₃ |
| F | —N(SO₂CH₃)₂ | Cl | CF₂Cl | C₂H₅ |
| F | —N(SO₂CH₃)(SO₂C₂H₅) | Cl | CF₂Cl | CH₃ |
| F | —N(SO₂C₂H₅)₂ | Cl | CF₂Cl | CH₃ |
| F | —N(SO₂CH₃)(SO₂C₃H₇) | Cl | CF₂Cl | CH₃ |
| F | —N(SO₂C₃H₇)₂ | Cl | CF₂Cl | CH₃ |
| F | —N(SO₂CH₃)(SO₂C₃H₇-i) | Cl | CF₂Cl | CH₃ |
| F | —N(SO₂C₃H₇-i)₂ | Cl | CF₂Cl | CH₃ |
| F | —N(SO₂C₂H₅)(SO₂C₃H₇) | Cl | CF₂Cl | CH₃ |
| F | SO₂CH₃–N(CH₃)–SO₂-cyclopropyl | Cl | CF₂Cl | CH₃ |
| F | SO₂-cyclopropyl–N(CH₃)–SO₂-cyclopropyl | Cl | CF₂Cl | CH₃ |
| F | —N(SO₂CH₃)(SO₂C₄H₉) | Cl | CF₂Cl | CH₃ |
| F | —N(SO₂C₄H₉)₂ | Cl | CF₂Cl | CH₃ |
| F | —N(SO₂CH₃)(SO₂CF₃) | Cl | CF₂Cl | CH₃ |
| F | —N(SO₂CF₃)₂ | Cl | CF₂Cl | CH₃ |
| F | —N(SO₂CH₃)(SO₂CH₂CF₃) | Cl | CF₂Cl | CH₃ |
| F | —N(SO₂CH₂CF₃)₂ | Cl | CF₂Cl | CH₃ |
| F | —N(SO₂CH₃)(SO₂C₃H₆Cl) | Cl | CF₂Cl | CH₃ |
| F | —N(SO₂CH₂CH₂CH₂Cl)₂ | Cl | CF₂Cl | CH₃ |
| F | —N(SO₂CH₃)(SO₂C₆H₅) | Cl | CF₂Cl | CH₃ |
| F | —N(SO₂C₆H₅)₂ | Cl | CF₂Cl | CH₃ |
| F | —N(SO₂C₂H₅)(SO₂C₆H₅) | Cl | CF₂Cl | CH₃ |

TABLE 1-continued

Examples of the compounds of the formula (I) or (IA)

| R¹ | R² | R³ | R⁴ | R⁵ |
|---|---|---|---|---|
| F | N(SO₂CH₃)(SO₂-C₆H₄-CH₃) (phenyl with SO₂ linker, methyl substituent) | Cl | CF₂Cl | CH₃ |
| F | —N(SO₂CH₃)₂ | H | CF₃ | C₂H₅ |
| F | —N(SO₂CH₃)(SO₂C₂H₅) | H | CF₃ | C₂H₅ |
| F | —N(SO₂C₂H₅)₂ | H | CF₃ | C₂H₅ |
| F | —N(SO₂CH₃)(SO₂C₃H₇) | H | CF₃ | C₂H₅ |
| F | —N(SO₂C₃H₇)₂ | H | CF₃ | C₂H₅ |
| F | —N(SO₂CH₃)(SO₂C₃H₇-i) | H | CF₃ | C₂H₅ |
| F | —N(SO₂C₃H₇-i)₂ | H | CF₃ | C₂H₅ |
| F | —N(SO₂C₂H₅)(SO₂C₃H₇) | H | CF₃ | C₂H₅ |
| F | N(SO₂CH₃)(SO₂-cyclopropyl) | H | CF₃ | C₂H₅ |
| F | N(SO₂-cyclopropyl)₂ | H | CF₃ | C₂H₅ |
| F | —N(SO₂CH₃)(SO₂C₄H₉) | H | CF₃ | C₂H₅ |
| F | —N(SO₂C₄H₉)₂ | H | CF₃ | C₂H₅ |
| F | —N(SO₂CH₃)(SO₂CF₃) | H | CF₃ | C₂H₅ |
| F | —N(SO₂CF₃)₂ | H | CF₃ | C₂H₅ |
| F | —N(SO₂CH₃)(SO₂CH₂CF₃) | H | CF₃ | C₂H₅ |
| F | —N(SO₂CH₂CF₃)₂ | H | CF₃ | C₂H₅ |
| F | —N(SO₂CH₃)(SO₂C₃H₆Cl) | H | CF₃ | C₂H₅ |
| F | —N(SO₂CH₂CH₂CH₂Cl)₂ | H | CF₃ | C₂H₅ |
| F | —N(SO₂CH₃)(SO₂C₆H₅) | H | CF₃ | C₂H₅ |
| F | —N(SO₂C₆H₅)₂ | H | CF₃ | C₂H₅ |
| F | —N(SO₂C₂H₅)(SO₂C₆H₅) | H | CF₃ | C₂H₅ |
| F | N(SO₂CH₃)(SO₂-C₆H₄-CH₃) | H | CF₃ | C₂H₅ |
| F | —N(SO₂CH₃)(SO₂C₂H₅) | H | CF₂Cl | C₂H₅ |
| F | N(SO₂CH₃)(SO₂-cyclopropyl) | H | CF₂Cl | C₂H₅ |
| F | N(SO₂-cyclopropyl)₂ | H | CF₂Cl | C₂H₅ |
| F | —N(SO₂CH₃)(SO₂C₄H₉) | H | CF₂Cl | C₂H₅ |
| F | —N(SO₂C₄H₉)₂ | H | CF₂Cl | C₂H₅ |
| F | —N(SO₂CH₃)(SO₂CF₃) | H | CF₂Cl | C₂H₅ |
| F | —N(SO₂CF₃)₂ | H | CF₂Cl | C₂H₅ |
| F | —N(SO₂CH₃)(SO₂CH₂CF₃) | H | CF₂Cl | C₂H₅ |
| F | —N(SO₂CH₂CF₃)₂ | H | CF₂Cl | C₂H₅ |
| F | —N(SO₂CH₃)(SO₂C₃H₆Cl) | H | CF₂Cl | C₂H₅ |
| F | —N(SO₂CH₂CH₂CH₂Cl)₂ | H | CF₂Cl | C₂H₅ |
| F | —N(SO₂CH₃)(SO₂C₆H₅) | H | CF₂Cl | C₂H₅ |
| F | —N(SO₂C₆H₅)₂ | H | CF₂Cl | C₂H₅ |
| F | —N(SO₂C₂H₅)(SO₂C₆H₅) | H | CF₂Cl | C₂H₅ |
| F | N(SO₂CH₃)(SO₂-C₆H₄-CH₃) | H | CF₂Cl | C₂H₅ |
| F | —N(SO₂CH₃)₂ | H | CF₃ | cyclopropyl |
| F | —N(SO₂CH₃)(SO₂C₂H₅) | H | CF₃ | cyclopropyl |
| F | —N(SO₂C₂H₅)₂ | H | CF₃ | cyclopropyl |
| F | —N(SO₂CH₃)(SO₂C₃H₇) | H | CF₃ | cyclopropyl |
| F | —N(SO₂C₃H₇)₂ | H | CF₃ | cyclopropyl |
| F | —N(SO₂CH₃)(SO₂C₃H₇-i) | H | CF₃ | cyclopropyl |
| F | —N(SO₂C₃H₇-i)₂ | H | CF₃ | cyclopropyl |
| F | —N(SO₂C₂H₅)(SO₂C₃H₇) | H | CF₃ | cyclopropyl |
| F | N(SO₂CH₃)(SO₂-cyclopropyl) | H | CF₃ | cyclopropyl |
| F | N(SO₂-cyclopropyl)₂ | H | CF₃ | cyclopropyl |
| F | —N(SO₂CH₃)(SO₂C₄H₉) | H | CF₃ | cyclopropyl |
| F | —N(SO₂C₄H₉)₂ | H | CF₃ | cyclopropyl |
| F | —N(SO₂CH₃)(SO₂CF₃) | H | CF₃ | cyclopropyl |
| F | —N(SO₂CF₃)₂ | H | CF₃ | cyclopropyl |
| F | —N(SO₂CH₃)(SO₂CH₂CF₃) | H | CF₃ | cyclopropyl |
| F | —N(SO₂CH₂CF₃)₂ | H | CF₃ | cyclopropyl |
| F | —N(SO₂CH₃)(SO₂C₃H₆Cl) | H | CF₃ | cyclopropyl |
| F | —N(SO₂CH₂CH₂CH₂Cl)₂ | H | CF₃ | cyclopropyl |
| F | —N(SO₂CH₃)(SO₂C₆H₅) | H | CF₃ | cyclopropyl |

TABLE 1-continued

Examples of the compounds of the formula (I) or (IA)

| R¹ | R² | R³ | R⁴ | R⁵ |
|---|---|---|---|---|
| F | —N(SO₂C₆H₅)₂ | H | CF₃ |  |
| F | —N(SO₂C₂H₅)(SO₂C₆H₅) | H | CF₃ |  |
| F | 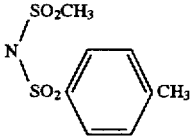 | H | CF₃ |  |
| F | —N(SO₂CH₃)₂ | H | CF₂Cl |  |
| F | —N(SO₂CH₃)(SO₂C₂H₅) | H | CF₂Cl |  |
| F | —N(SO₂C₂H₅)₂ | H | CF₂Cl |  |
| F | —N(SO₂CH₃)(SO₂C₃H₇) | H | CF₂Cl |  |
| F | —N(SO₂C₃H₇)₂ | H | CF₂Cl |  |
| F | —N(SO₂CH₃)(SO₂C₃H₇-i) | H | CF₂Cl |  |
| F | —N(SO₂C₃H₇-i)₂ | H | CF₂Cl |  |
| F | —N(SO₂C₂H₅)(SO₂C₃H₇) | H | CF₂Cl |  |
| F | 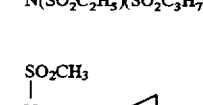 | H | CF₂Cl |  |
| F | 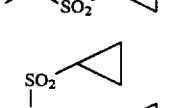 | H | CF₂Cl |  |
| F | —N(SO₂CH₃)(SO₂C₄H₉) | H | CF₂Cl |  |
| F | —N(SO₂C₄H₉)₂ | H | CF₂Cl |  |
| F | —N(SO₂CH₃)(SO₂CF₃) | H | CF₂Cl |  |
| F | —N(SO₂CF₃)₂ | H | CF₂Cl |  |
| F | —N(SO₂CH₃)(SO₂CH₂CF₃) | H | CF₂Cl |  |
| F | —N(SO₂CH₂CF₃)₂ | H | CF₂Cl |  |
| F | —N(SO₂CH₃)(SO₂C₃H₆Cl) | H | CF₂Cl |  |
| F | —N(SO₂CH₂CH₂CH₂Cl)₂ | H | CF₂Cl |  |
| F | —N(SO₂CH₃)(SO₂C₆H₅) | H | CF₂Cl |  |
| F | —N(SO₂C₆H₅)₂ | H | CF₂Cl |  |
| F | —N(SO₂C₂H₅)(SO₂C₆H₅) | H | CF₂Cl |  |
| F | 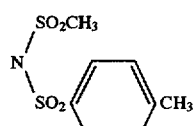 | H | CF₂Cl |  |
| F | —N(SO₂CH₃)(COOCH₃) | H | CF₃ | CH₃ |
| F | —N(SO₂CH₃)(COOC₂H₅) | H | CF₃ | CH₃ |
| F | —N(SO₂CH₃)(COOC₄H₉-t) | H | CF₃ | CH₃ |
| F | —N(SO₂CH₃)(COOC₆H₅) | H | CF₃ | CH₃ |
| F | —N(SO₂CH₃)(COCH₃) | H | CF₃ | CH₃ |
| F | —N(SO₂CH₃)(COCF₃) | H | CF₃ | CH₃ |
| F | —N(SO₂CH₃)(CHO) | H | CF₃ | CH₃ |
| F | 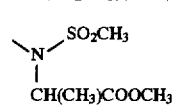 | H | CF₃ | CH₃ |
| F | 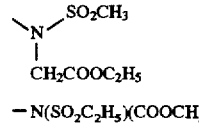 | H | CF₃ | CH₃ |
| F | —N(SO₂C₂H₅)(COOCH₃) | H | CF₃ | CH₃ |
| F | —N(SO₂C₂H₅)(COOC₂H₅) | H | CF₃ | CH₃ |
| F | —N(SO₂C₂H₅)(COOC₄H₉-t) | H | CF₃ | CH₃ |
| F | —N(SO₂C₂H₅)(COOC₆H₅) | H | CF₃ | CH₃ |
| F | —N(SO₂C₂H₅)(COCH₃) | H | CF₃ | CH₃ |
| F | —N(SO₂C₂H₅)(COCF₃) | H | CF₃ | CH₃ |
| F | —N(SO₂C₂H₅)(CHO) | H | CF₃ | CH₃ |
| F | —N(SO₂C₂H₅)(CH₂COOC₂H₅) | H | CF₃ | CH₃ |
| F | —N(SO₂C₃H₇)(COOCH₃) | H | CF₃ | CH₃ |
| F | —N(SO₂C₃H₇)(COOC₂H₅) | H | CF₃ | CH₃ |
| F | —N(SO₂C₃H₇)(COOC₄H₉-t) | H | CF₃ | CH₃ |
| F | —N(SO₂C₃H₇)(COOC₆H₅) | H | CF₃ | CH₃ |
| F | —N(SO₂C₃H₇)(COCH₃) | H | CF₃ | CH₃ |
| F | —N(SO₂C₃H₇)(COCF₃) | H | CF₃ | CH₃ |
| F | —N(SO₂C₃H₇)(CHO) | H | CF₃ | CH₃ |
| F | —N(SO₂C₃H₇)(CH₂COOC₂H₅) | H | CF₃ | CH₃ |
| F | —N(SO₂C₄H₉)(COOCH₃) | H | CF₃ | CH₃ |
| F | —N(SO₂C₄H₉)(COOC₂H₅) | H | CF₃ | CH₃ |
| F | —N(SO₂C₄H₉)(COOC₄H₉-t) | H | CF₃ | CH₃ |
| F | —N(SO₂C₄H₉)(COOC₆H₅) | H | CF₃ | CH₃ |
| F | —N(SO₂C₄H₉)(COCH₃) | H | CF₃ | CH₃ |
| F | —N(SO₂C₄H₉)(COCF₃) | H | CF₃ | CH₃ |
| F | —N(SO₂C₄H₉)(CHO) | H | CF₃ | CH₃ |
| F | —N(SO₂C₄H₉)(CH₂COOC₂H₅) | H | CF₃ | CH₃ |
| F | —N(SO₂C₄H₉)(CH₂COOC₂H₅) | H | CF₃ | CH₃ |
| F | —N(SO₂CH₂CF₃)(COOCH₃) | H | CF₃ | CH₃ |
| F | —N(SO₂CH₂CF₃)(COOC₂H₅) | H | CF₃ | CH₃ |
| F | —N(SO₂CH₂CF₃)(COOC₄H₉-t) | H | CF₃ | CH₃ |
| F | —N(SO₂CH₂CF₃)(COOC₆H₅) | H | CF₃ | CH₃ |
| F | —N(SO₂CH₂CF₃)(COCH₃) | H | CF₃ | CH₃ |
| F | —N(SO₂CH₂CF₃)(COCF₃) | H | CF₃ | CH₃ |
| F | —N(SO₂CH₂CF₃)(CHO) | H | CF₃ | CH₃ |
| F | —N(SO₂CH₂CF₃)(CH₂COOCH3) | H | CF₃ | CH₃ |
| F | —N(SO₂C₆H₅)(COOCH₃) | H | CF₃ | CH₃ |
| F | —N(SO₂C₆H₅)(COOC₂H₅) | H | CF₃ | CH₃ |
| F | —N(SO₂C₆H₅)(COOC₄H₉-t) | H | CF₃ | CH₃ |
| F | —N(SO₂C₆H₅)(COOC₆H₅) | H | CF₃ | CH₃ |

TABLE 1-continued

Examples of the compounds of the formula (I) or (IA)

| $R^1$ | $R^2$ | $R^3$ | $R^4$ | $R^5$ |
|---|---|---|---|---|
| F | $-N(SO_2C_6H_5)(COCH_3)$ | H | $CF_3$ | $CH_3$ |
| F | $-N(SO_2C_6H_5)(COCF_3)$ | H | $CF_3$ | $CH_3$ |
| F | $-N(SO_2C_6H_5)(CHO)$ | H | $CF_3$ | $CH_3$ |
| F | $-N(SO_2C_6H_5)(CH_2COOC_2H_5)$ | H | $CF_3$ | $CH_3$ |
| F | $-N(SO_2CH_3)(COOCH_3)$ | H | $CHF_2$ | $CH_3$ |
| F | $-N(SO_2C_2H_5)(COOCH_3)$ | H | $CHF_2$ | $CH_3$ |
| F | $-N(SO_2CH_3)(COOC_2H_5)$ | H | $CHF_2$ | $CH_3$ |
| F | $-N(SO_2CH_3)(COOCH_3)$ | H | $CClF_2$ | $CH_3$ |
| F | $-N(SO_2C_2H_5)(COOCH_3)$ | H | $CClF_2$ | $CH_3$ |
| F | $-N(SO_2CH_3)(COOC_2H_5)$ | H | $CClF_2$ | $CH_3$ |
| H | $-N(SO_2CH_3)_2$ | H | $CF_3$ | $NH_2$ |
| H | $-N(SO_2CH_3)(SO_2C_2H_5)$ | H | $CF_3$ | $NH_2$ |
| H | $-N(SO_2C_2H_5)_2$ | H | $CF_3$ | $NH_2$ |
| H | $-N(SO_2CH_3)(SO_2C_3H_7)$ | H | $CF_3$ | $NH_2$ |
| H | $-N(SO_2C_3H_7)_2$ | H | $CF_3$ | $NH_2$ |
| H | $-N(SO_2CH_3)(SO_2C_3H_7\text{-i})$ | H | $CF_3$ | $NH_2$ |
| H | $-N(SO_2C_3H_7\text{-i})_2$ | H | $CF_3$ | $NH_2$ |
| F | $-N(SO_2CH_3)_2$ | H | $CF_3$ | $NH_2$ |
| F | $-N(SO_2CH_3)(SO_2C_2H_5)$ | H | $CF_3$ | $NH_2$ |
| F | $-N(SO_2C_2H_5)_2$ | H | $CF_3$ | $NH_2$ |
| F | $-N(SO_2CH_3)(SO_2C_3H_7)$ | H | $CF_3$ | $NH_2$ |
| F | $-N(SO_2C_3H_7)_2$ | H | $CF_3$ | $NH_2$ |
| F | $-N(SO_2CH_3)(SO_2C_3H_7\text{-i})$ | H | $CF_3$ | $NH_2$ |
| F | $-N(SO_2C_3H_7\text{-i})_2$ | H | $CF_3$ | $NH_2$ |
| F | $-N(SO_2C_2H_5)(SO_2C_3H_7)$ | H | $CF_3$ | $NH_2$ |
| F | 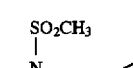 | H | $CF_3$ | $NH_2$ |
| F | 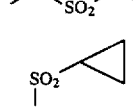 | H | $CF_3$ | $NH_2$ |
| F | $-N(SO_2CH_3)(SO_2C_4H_9)$ | H | $CF_3$ | $NH_2$ |
| F | $-N(SO_2C_4H_9)_2$ | H | $CF_3$ | $NH_2$ |
| F | $-N(SO_2CH_3)(SO_2CF_3)$ | H | $CF_3$ | $NH_2$ |
| F | $-N(SO_2CF_3)_2$ | H | $CF_3$ | $NH_2$ |
| F | $-N(SO_2CH_3)(SO_2CH_2CF_3)$ | H | $CF_3$ | $NH_2$ |
| F | $-N(SO_2CH_2CF_3)_2$ | H | $CF_3$ | $NH_2$ |
| F | $-N(SO_2CH_2Cl)_2$ | H | $CF_3$ | $NH_2$ |
| F | $-N(SO_2CH_2CH_2CH_2Cl)_2$ | H | $CF_3$ | $NH_2$ |
| F | $-N(SO_2CH_3)(SO_2C_6H_5)$ | H | $CF_3$ | $NH_2$ |
| F | $-N(SO_2C_6H_5)_2$ | H | $CF_3$ | $NH_2$ |
| F | $-N(SO_2C_2H_5)(SO_2C_6H_5)$ | H | $CF_3$ | $NH_2$ |
| F | $-N(SO_2CH_3)_2$ | H | $CHF_2$ | $NH_2$ |
| F | $-N(SO_2CH_3)(SO_2C_2H_5)$ | H | $CHF_2$ | $NH_2$ |
| F | $-N(SO_2C_2H_5)_2$ | H | $CHF_2$ | $NH_2$ |
| F | $-N(SO_2CH_3)(SO_2C_3H_7)$ | H | $CHF_2$ | $NH_2$ |
| F | $-N(SO_2C_3H_7)_2$ | H | $CHF_2$ | $NH_2$ |
| F | $-N(SO_2CH_3)(SO_2C_3H_7\text{-i})$ | H | $CHF_2$ | $NH_2$ |
| F | $-N(SO_2C_3H_7\text{-i})_2$ | H | $CHF_2$ | $NH_2$ |
| F | $-N(SO_2C_2H_5)(SO_2C_3H_7)$ | H | $CHF_2$ | $NH_2$ |
| F | 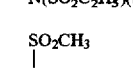 | H | $CHF_2$ | $NH_2$ |
| F | $-N(SO_2CH_3)_2$ | H | $CF_2Cl$ | $NH_2$ |
| F | $-N(SO_2CH_3)(SO_2C_2H_5)$ | H | $CF_2Cl$ | $NH_2$ |
| F | $-N(SO_2C_2H_5)_2$ | H | $CF_2Cl$ | $NH_2$ |
| F | $-N(SO_2CH_3)(SO_2C_3H_7)$ | H | $CF_2Cl$ | $NH_2$ |
| F | $-N(SO_2C_3H_7)_2$ | H | $CF_2Cl$ | $NH_2$ |
| F | $-N(SO_2CH_3)(SO_2C_3H_7\text{-i})$ | H | $CF_2Cl$ | $NH_2$ |
| F | $-N(SO_2C_3H_7\text{-i})_2$ | H | $CF_2Cl$ | $NH_2$ |
| F | $-N(SO_2C_2H_5)(SO_2C_3H_7)$ | H | $CF_2Cl$ | $NH_2$ |
| F | $-N(SO_2CH_3)(SO_2C_2H_5)$ | H | $C_2F_5$ | $NH_2$ |
| F | $-N(SO_2C_2H_5)_2$ | H | $C_2F_5$ | $NH_2$ |
| F | $-N(SO_2CH_3)(SO_2C_3H_7)$ | H | $C_2F_5$ | $NH_2$ |
| F | $-N(SO_2C_3H_7)_2$ | H | $C_2F_5$ | $NH_2$ |
| F | $-N(SO_2CH_3)(SO_2C_3H_7\text{-i})$ | H | $C_2F_5$ | $NH_2$ |
| F | $-N(SO_2C_3H_7\text{-i})_2$ | H | $C_2F_5$ | $NH_2$ |
| F | $-N(SO_2C_2H_5)(SO_2C_3H_7)$ | H | $C_2F_5$ | $NH_2$ |
| Cl | $-N(SO_2CH_3)_2$ | H | $CF_3$ | $NH_2$ |
| Cl | $-N(SO_2CH_3)(SO_2C_2H_5)$ | H | $CF_3$ | $NH_2$ |
| Cl | $-N(SO_2CH_3)_2$ | F | $CF_3$ | $NH_2$ |
| Cl | $-N(SO_2CH_3)(SO_2C_2H_5)$ | F | $CF_3$ | $NH_2$ |
| F | $-N(SO_2CH_3)_2$ | Cl | $CF_3$ | $NH_2$ |
| F | $-N(SO_2CH_3)(SO_2C_2H_5)$ | Cl | $CF_3$ | $NH_2$ |
| F | $-N(SO_2CH_3)_2$ | $CH_3$ | $CF_3$ | $NH_2$ |
| F | $-N(SO_2CH_3)(SO_2C_2H_5)$ | $CH_3$ | $CF_3$ | $NH_2$ |
| F | $-N(SO_2CH_3)_2$ | H | $CF_3$ | OH |
| F | $-N(SO_2CH_3)(SO_2C_2H_5)$ | H | $CHF_2$ | OH |
| F | $-N(SO_2CH_3)_2$ | H | $CF_2Cl$ | OH |
| F | $-N(SO_2CH_3)(SO_2C_2H_5)$ | H | $C_2F_5$ | OH |

If, for example, methyl 3-amino-crotonate and N-methoxycarbonyl-N-(2-cyano4-fluoro-5-isocyanato-phenyl)-methanesulphonamide are used as starting substances, the course of the reaction in process (a) according to the invention can be outlined by the following equation:

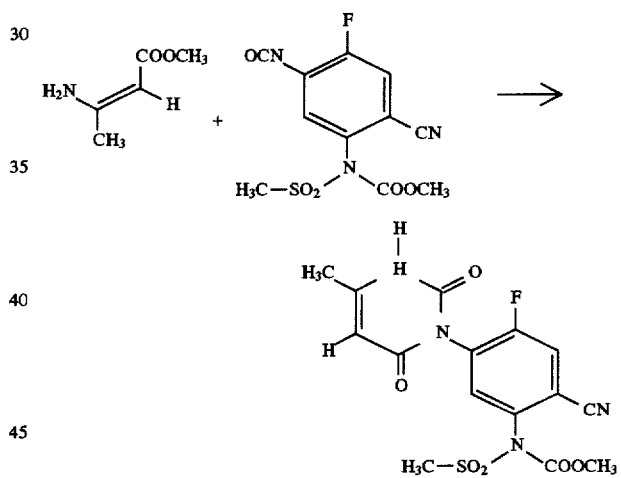

If, for example, 1-[2-chloro-4-cyano-5-(N,N-bis-methylsulphonyl)-amino-phenyl]-3,6-dihydro-2,6-dioxo4-trifluoromethyl-1(2H)-pyrimidine and methyl bromide are used as starting substances, the course of the reaction in process (b) according to the invention can be outlined by the following equation:

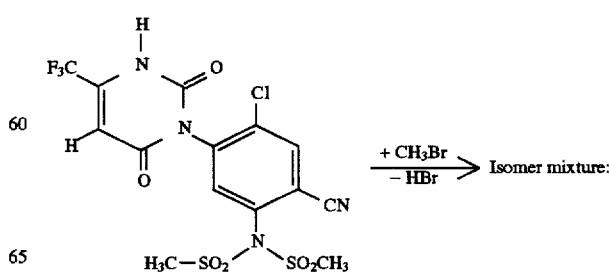

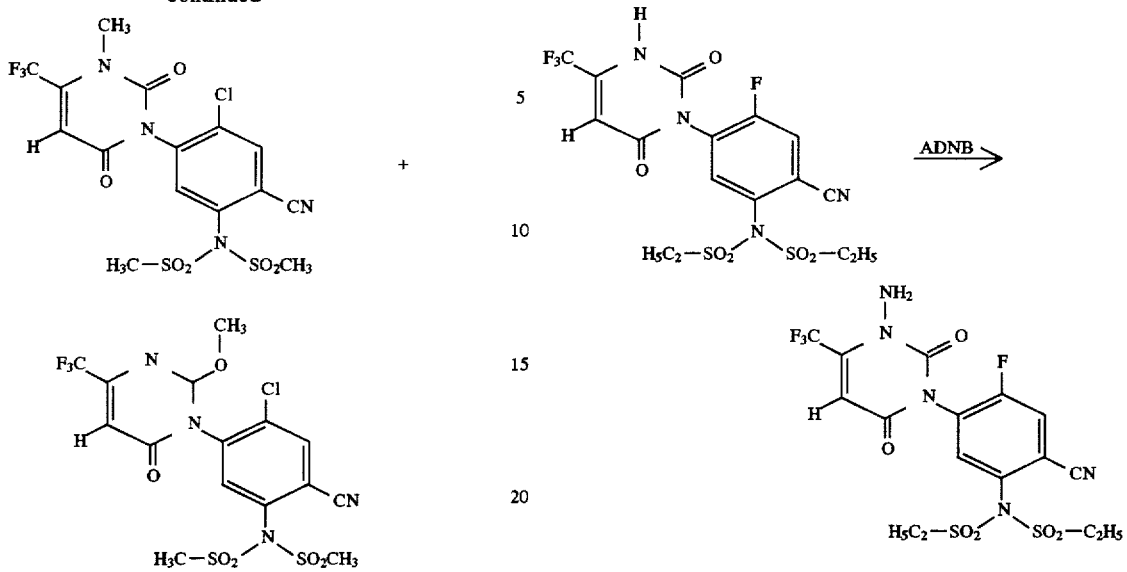

If, for example, 1-(4-cyano-2-fluoro-5-ethylsulphonylamino-phenyl)-3,6-dihydro-3,4-dimethyl-2,6-dioxo-1(2H)-pyrimidine and methanesulphonyl chloride are used as starting substances, the course of the reaction in process (c) according to the invention can be outlined by the following equation:

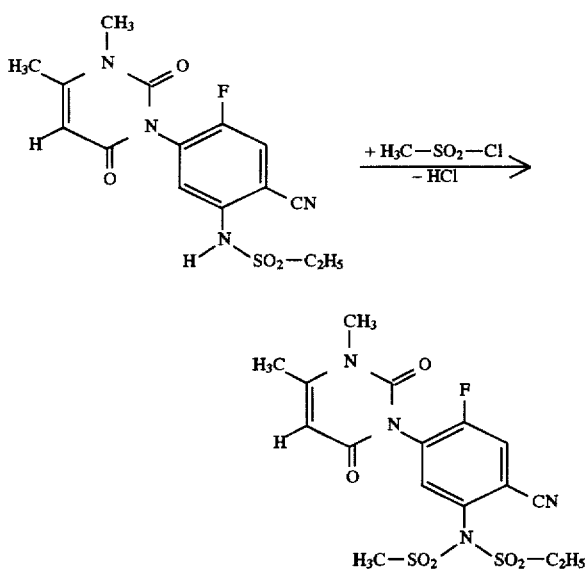

If, for example, 1-[2-fluoro-4-cyano-5-(N,N-bis-methylsulphonyl)-amino-phenyl]-3,6-dihydro-2,6-dioxo-4-trifluoromethyl-1(2H)-pyrimidine and 1-aminooxy-2,4-dinitrobenzene (ADNB) are used as starting substances, the course of the reaction in process (d) according to the invention can be outlined by the following equation:

Formula (II) provides a general definition of the aminoalkenoic esters to be used as starting substances in process (a) according to the invention for the preparation of compounds of the formula (I). In formula (II), $R^3$ and $R^4$ preferably, or in particular, have the meaning which has already been mentioned above in connection with the description of the compounds of the formula (I) according to the invention as being preferred, or particularly preferred, for $R^3$ and $R^4$; R preferably represents $C_1$-$C_4$-alkyl, phenyl or benzyl, in particular methyl or phenyl.

The starting substances of the formula (II) are known and/or can be prepared by processes known per se (cf. J. Heterocycl. Chem. 9 (1972), 513–522).

Formula (III) provides a general definition of the cyanoaryl isocyanates furthermore to be used as starting substances in process (a) according to the invention. In formula (III), $R^1$ and $R^2$ preferably, or in particular, have the meanings which have already been mentioned above in connection with the description of the compounds of the formula (I) according to the invention as being preferred, or particularly preferred, for $R^1$ and $R^2$.

The cyanoaryl isocyanates of the general formula (III) were hitherto not known from the literature; however, they are the subject-matter of an earlier application (cf. DE 4 327 743).

The cyanoaryl isocyanates of the formula (III) are obtained when cyanoarylamines of the general formula (VIII)

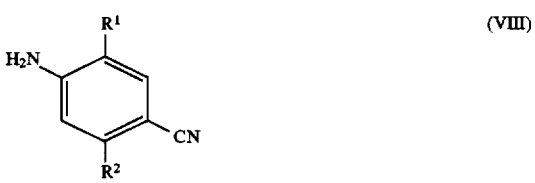

in which $R^1$ and $R^2$ have the abovementioned meanings are reacted with phosgene in the presence of a diluent, such as, for example, chlorobenzene, at temperatures between −20° C. and +150° C. (cf. the preparation examples).

Formula (IV) provides a general definition of the cyanoarylurethanes optionally to be used as starting substances in process (a) according to the invention. In formula (IV), $R^1$ and $R^2$ preferably, or in particular, have the meanings which have already been mentioned above in connection with the description of the compounds of the formula (I) as being preferred, or particularly preferred, for $R^1$ and $R^2$; $R^2$ preferably represents $C_1$–$C_4$-alkyl, phenyl or benzyl, in particular methyl or phenyl.

The cyanoarylurethanes of the general formula (IV) were hitherto unknown from the literature; however, they are the subject-matter of an earlier application (cf. DE 4 327 743).

Cyanoarylurethanes of the formula (IV) are obtained when cyanoarylamines of the general formula (VIII)—above—are reacted with chlorocarbonyl compounds of the general formula (IX)

RO—CO—Cl    (IX)

in which

R has the abovementioned meaning, at temperatures between 0° C. and 100° C., if appropriate in the presence of an acid acceptor, such as, for example, pyridine, and, if appropriate, in the presence of a diluent, such as, for example, methylene chloride (cf. the preparation examples).

Process (a) according to the invention for the preparation of the new N-cyanoaryl nitrogen heterocycles of the formula (I) is preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide tetramethylene sulphone and hexamethylphosphoric triamide.

Process (a) according to the invention is preferably carried out in the presence of a reaction auxiliary. Suitable reaction auxiliaries are mainly acid acceptors. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate or sodium hydrogen carbonate, and potassium carbonate or potassium hydrogen carbonate, and calcium carbonate, alkali metal acetates, such as sodium acetate and potassium acetate, alkali metal alcoholates, such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (a) according to the invention, the reaction temperatures can be varied within a substantial range. In general, the process is carried out at temperatures between −120° C. and +100° C., preferably at temperatures between −70° C. and +80° C.

Process (a) according to the invention is generally carried out under atmospheric pressure. However, it is also possible to carry out the process under elevated or reduced pressure.

To carry out process (a) according to the invention, the starting substances required in each case are generally employed in approximately equimolar amounts. However, it is also possible to use one of the two reactants employed in each case in a larger excess. The reactions are generally carried out in a suitable diluent in the presence of a reaction auxiliary, and the reaction mixture is stirred for several hours at the temperature required in each case. Working-up in process (a) according to the invention is carried out in each case by customary methods.

Formulae (IA) and (IB)—with the proviso that $R^5$ in these formulae represents hydrogen—provide a general definition of the N-cyanoaryl nitrogen heterocycles to be used as starting substances in process (b) according to the invention for the preparation of compounds of the formula (I). In formulae (IA) and (IB), $R^1$, $R^2$, $R^3$ and $R^4$ preferably, or in particular, have the meanings which have already been mentioned above in connection with the description of the compounds of the formula (I) according to the invention as being preferred, or particularly preferred, for $R^1$, $R^2$, $R^3$ and $R^4$.

The starting substances of the formulae (IA) and (IB) for process (b) are new compounds according to the invention; they can be prepared by process (a) according to the invention.

Formulae (IV) and (V) provide general definitions of the alkylating agents furthermore to be used as starting substances in process (b) according to the invention. In formulae (IV) and (V), $R^5$ preferably, or in particular, has the meaning which has already been mentioned above in connection with the description of the compounds of the formula (I) according to the invention as being preferred, or particularly preferred, for $R^5$.

The starting substances of the formulae (IV) and (V) are known organic chemicals for synthesis.

Process (b) according to the invention is preferably carried out using a diluent. Suitable diluents are mainly those which have already been mentioned in the description of process (a) according to the invention.

Acid acceptors which can be used in process (b) according to the invention are all acid-binding agents which can conventionally be used for such reactions. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate or sodium hydrogen carbonate, and potassium carbonate or potassium hydrogen carbonate, and also calcium carbonate, alkali metal acetates, such as sodium acetate and potassium acetate, alkali metal alcoholates, such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (b) according to the invention, the reaction temperatures can be varied within a substantial range. In general, the process is carried out at temperatures between 0° C. and 120° C., preferably at temperatures between 10° C. and 100° C.

Process (b) according to the invention is generally carried out under atmospheric pressure. However, it is also possible to carry out the process under elevated or reduced pressure.

To carry out process (b) according to the invention, the starting substances required in each case are generally employed in approximately equimolar amounts. However, it is also possible to use a larger excess of one of the two reactants employed in each case. The reactions are generally carried out in a suitable diluent in the presence of an acid acceptor, and the reaction mixture is stirred for several hours at the temperature required in each case. Working-up in process (b) is carried out in each case by customary methods (cf. the preparation examples).

Formula (I)—with the proviso that, in this formula, $R^2$ represents the group —NH—$SO_2$—$A^1$—provides a general definition of the N-cyanoaryl nitrogen heterocycles to be used as starting substances in process (c) according to the invention for the preparation of compounds of the formula (I). In formula (I), $A^1$, $R^1$, $R^3$, $R^4$ and Z then preferably, or in particular, have those meanings which have already been mentioned above in connection with the description of the compounds of the formula (I) according to the invention as being preferred, or particularly preferred, for $A^1$, $R^1$, $R^3$, $R^4$ and Z.

The starting substances of the formula (I) for process (c) are the subject-matter of earlier applications (cf. DE 4 327 743; cf. also U.S. Pat. No. 5,084,084; preparation examples).

Formula (VII) provides a general definition of the halogen compounds furthermore to be used as starting substances in process (c) according to the invention. In formula (VII), n, $A^2$ and $A^3$ preferably, or in particular, have the meaning which has already been mentioned above in connection with the description of the compounds of the formula (I) according to the invention as being preferred, or particularly preferred, for n, $A^2$ and $A^3$; $X^2$ preferably represents fluorine, chlorine or bromine, in particular chlorine.

The starting substances of the formula (VI) are known organic chemicals for synthesis.

Process (c) according to the invention is preferably carried out using a diluent. Suitable diluents are, in particular, those which have already been mentioned in the description of process (a) according to the invention.

If appropriate, process (c) according to the invention is carried out in the presence of an acid acceptor. Suitable acid acceptors are those which have already been mentioned in the description of process (b) according to the invention.

When carrying out process (c) according to the invention, the reaction temperatures can be varied within a substantial range. In general, the process is carried out at temperatures between 0° C. and 150° C., preferably at temperatures between 20° C. and 120° C.

Process (c) according to the invention is generally carried out under atmospheric pressure. However, it is also possible to carry out the process under elevated or reduced pressure.

To carry out process (c) according to the invention, the starting substances required in each case are generally employed in approximately equimolar amounts. However, it is also possible to use a larger excess of one of the two reactants employed in each case. The reactions are generally carried out in a suitable diluent in the presence of an acid acceptor, and the reaction mixture is stirred for several hours at the temperature required in each case. Working-up in process (c) is carried out in each case by customary methods (cf. the preparation examples).

Formulae (IA) and (IB)—with the proviso that, in these formulae, $R^5$ represents hydrogen—provide general definitions of the N-cyanoaryl nitrogen heterocycles to be used as starting substances in process (d) according to the invention for the preparation of compounds of the formula (I). In formulae (IA) and (IB), $R^1$, $R^2$, $R^3$ and $R^4$ preferably, or in particular, have those meanings which have already been mentioned above in connection with the description of the compounds of the formula (I) according to the invention as being preferred, or particularly preferred, for $R^1$, $R^2$, $R^3$ and $R^4$.

The starting substances of the formulae (IA) and (IB) for process (c) are new compounds according to the invention; they can be prepared by process (a) according to the invention.

Process (d) according to the invention is carried out using an electrophilic animating or hydroxylating agent. The customary aminating or hydroxylating agents can be employed. Examples which may be mentioned are 1-aminooxy-2,4-dinitro-benzene, hydroxylamine-O-sulphonicacid, N-(dialkoxyphosphoryl)-O-(4-nitro-phenyl-sulphonyl) hydroxylamine and 3-chloro-perbenzoic acid. These are known chemicals for synthesis.

Process (d) according to the invention is preferably carried out using a diluent. Suitable diluents are mainly those which have already been mentioned in the description of process (a) according to the invention.

If appropriate, process (d) according to the invention is carried out in the presence of an acid acceptor. Suitable acid acceptors are those which have already been mentioned in the description of process (b) according to the invention.

When carrying out process (d) according to the invention, the reaction temperatures can be varied within a substantial range. In general, the process is carried out at temperatures between 0° C. and 150° C., preferably at temperatures between 10° C. and 80° C.

Process (d) according to the invention is generally carried out under atmospheric pressure. However, it is also possible to carry out the process under elevated or reduced pressure.

To carry out process (d) according to the invention, the starting substances required in each case are generally employed in approximately equimolar amounts. However, it is also possible to use a larger excess of one of the two reactants employed in each case. The reactions are generally carried out in a suitable diluent in the presence of an acid acceptor, and the reaction mixture is stirred for several hours at the temperature required in each case. Working-up in process (d) is carried out in each case by customary methods (cf. the preparation examples).

The N-cyanoaryl nitrogen heterocycles according to the invention can be employed for the preparation of compounds of the formula (I) in which $R^2$ represents the group —NH—SO$_2$—A$^1$.

The compounds of the formula (I) in which $R^2$ represents the group —NH—SO$_2$—A$^1$ are obtained when corresponding compounds of the formula (I) in which $R^1$, $R^2$, $R^3$, $R^4$ and Z have the abovementioned meaning are reacted with water in the presence of a reaction auxiliary, such as, for example, sodium acetate or potassium acetate, sodium hydrogen carbonate or potassium hydrogen carbonate, sodium carbonate, potassium carbonate or calcium carbonate, preferably sodium hydrogen carbonate, and, if appropriate, in the presence of an organic solvent, such as, for example, methanol, ethanol, n- or i-propanol, acetone, methyl ethyl ketone or methyl isobutyl ketone, preferably acetone, at temperatures between 0° C. and 100° C., preferably between 10° C. and 80° C., and the mixture is subsequently acidified using a strong acid, such as, for example, hydrochloric acid (cf. the preparation examples).

The compounds of the formula (I) which can thus be obtained are already known (cf. U.S. Pat. No. 5,084,084) or the subject-matter of an earlier application (cf. DE 4 327 743).

Surprisingly, the compounds of the formula (I) in which $R^2$ represents the group —NH—SO$_2$—A$^1$ can be obtained by the process described above in a considerably better yield and quality than by prior-art methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating dicotyledon weeds in monocotyledon and dicotyledon cultures, such as, for example, in wheat, maize and soya, by the pre- and the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxyphenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazine, cyanazine, simazine, simetryn, terbutryn and terbutylazine; triazinones such as, for example, hexazinone, metamitron and metribuzin; others such as, for example, arninotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

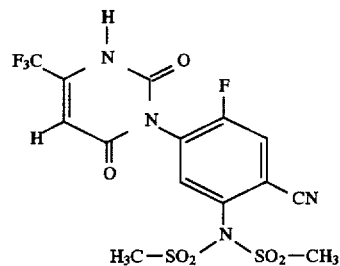

0.63 g (5 mmol) of methanesulphonyl chloride are added dropwise with stirring at 20° C. to a mixture of 1.96 g (5 mmol) of 1-(4-cyano-2-fluoro-5-methylsulphonylaminophenyl)-3,6-dihydro-2,6-dioxo-4-trifluoromethyl-1(2H)-pyrimidine, 0.61 g (6 mmol) of triethylamine and 20 ml of acetonitrile. The reaction mixture is stirred for 60 minutes at 20° C., a further 0.6 g of triethylamine and 0.5 g of methanesulphonyl chloride are added, and the mixture is stirred for a further 2 hours at 20° C. It is then concentrated, the residue is shaken with water/ethyl acetate, and the organic phase is separated off, dried using sodium sulphate and filtered. The filtrate is concentrated, the residue is digested using diethyl ether, and the product, which is obtained as crystals, is isolated by filtration.

2.1 g (90% of theory) of 1-[4-cyano-2-fluoro-5-(bis-methylsulphonyl-amino)-phenyl]-3,6-dihydro-2,6-dioxo-4-trifluoromethyl-1(2H)-pyrimidine of melting point 143° C. are obtained.

Example 2

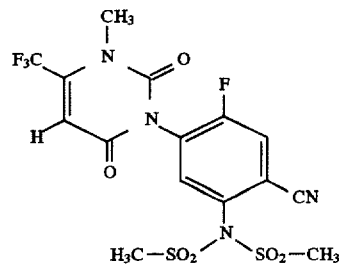

A mixture of 2.06 g (4.25 mmol) of 1-[4-cyano-2-fluoro-5-(bis-methylsulphonylamino)-phenyl]-3,6-dihydro-2,6-dioxo-4-trifluoromethyl-1(2H)-pyrimidine, 0.63 g (5.0 mmol) of dimethyl sulphate, 0.70 g (5.0 mmol) of potassium carbonate and 50 ml of acetone is refluxed for 2 hours and subsequently concentrated. The residue is digested with water and the product, which is obtained as crystals, is isolated by filtration.

1.8 g (87% of theory) of 1-[4-cyano-2-fluoro-5-(bis-methylsulphonyl-amino)-phenyl]-3,6-dihydro-2,6-dioxo-3-methyl-4-trifluoromethyl-1(2H)-pyrimidine of melting point 273° C. are obtained.

Compounds of the formula (I)—or of the formulae (IA) and (IB)—which can be prepared analogously to Examples 1 and 2 and following the general description of the preparation processes according to the invention are, for example, those listed in Table 2 below:

TABLE 2

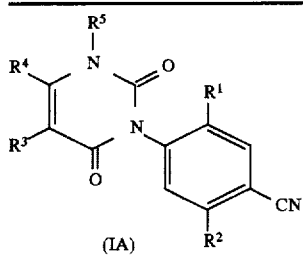

(IA)

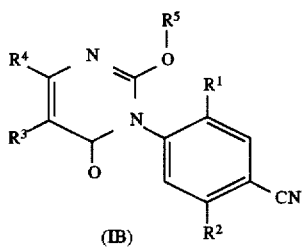

(IB)

Examples of the compounds of the formula (I)

| Ex. No. | Gen. formula | $R^1$ | $R^2$ | $R^3$ | $R^4$ | $R^5$ | Melting point (°C.) |
|---|---|---|---|---|---|---|---|
| 3 | IA | F | $-N(SO_2C_2H_5)_2$ | H | $CF_3$ | H | 155 |
| 4 | IA | F | $-N(SO_2C_2H_5)_2$ | H | $CF_3$ | $CH_3$ | 128 |
| 5 | IA | F | $-N(SO_2C_2H_5)_2$ | H | $CHF_2$ | H | 135 |
| 6 | IA | F | $-N(SO_2C_2H_5)_2$ | H | $CHF_2$ | $CH_3$ | 213 |
| 7 | IA | F | $-N(SO_2-CH_3)(SO_2-C_3H_7\text{-}n)$ | H | $CF_3$ | H | 115 |
| 8 | IA | F | $-N(SO_2C_3H_7)_2$ | H | $CF_3$ | H | 113 |
| 9 | IA | F | $-N(SO_2-CH_3)(SO_2-C_2H_5)$ | H | $CF_3$ | H | 79 |
| 10 | IA | F | $-N(SO_2-CH_3)(SO_2-C_2H_5)$ | H | $CF_3$ | $CH_3$ | 204 |
| 11 | IA | F | $-N(SO_2C_3H_7)_2$ | H | $CF_3$ | $CH_3$ | 245 |
| 12 | IA | F | $-N(SO_2-CH_3)(SO_2-C_3H_7\text{-}n)$ | H | $CF_3$ | $CH_3$ | 179 |
| 13 | IA | F | $-N(SO_2-CH_3)(COOC_2H_5)$ | H | $CF_3$ | $CH_3$ | 105 |
| 14 | IA | F | $-N(SO_2CH_3)_2$ | H | $CHF_2$ | H | 267 |
| 15 | IA | F | $-N(SO_2CH_3)_2$ | H | $CHF_2$ | $CH_3$ | 258 |
| 16 | IA | F | $-N(SO_2CH_3)_2$ | H | $CClF_2$ | H | 289 |
| 17 | IA | F | $-N(SO_2CH_3)_2$ | H | $CClF_2$ | $CH_3$ | 258 |
| 18 | IA | F | $-N(SO_2-CH_3)(SO_2\text{-cyclopropyl})$ | H | $CF_3$ | H | 277 |
| 19 | IA | F | $-N(SO_2-CH_3)(SO_2\text{-cyclopropyl})$ | H | $CF_3$ | $CH_3$ | 105 |
| 20 | IA | F | $-N(SO_2CH_3)_2$ | $CH_3$ | $CF_3$ | H | 243 |

TABLE 2-continued

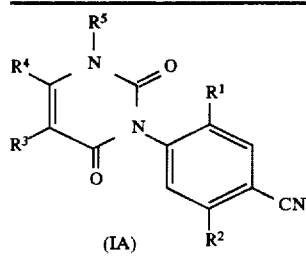

(IA)

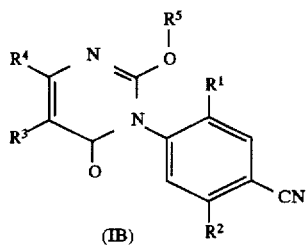

(IB)

Examples of the compounds of the formula (I)

| Ex. No. | Gen. formula | R¹ | R² | R³ | R⁴ | R⁵ | Melting point (°C.) |
|---|---|---|---|---|---|---|---|
| 21 | IA | F | $\underset{SO_2-CH(CH_3)_2}{N\!\!-\!\!SO_2-CH_3}$ | H | $CClF_2$ | H | 258 |
| 22 | IA | F | $\underset{SO_2-\triangleleft}{N\!\!-\!\!SO_2-CH_3}$ | H | $CClF_2$ | H | 105 |
| 23 | IA | F | $\underset{SO_2-CH(CH_3)_2}{N\!\!-\!\!SO_2-CH_3}$ | H | $CClF_2$ | $CH_3$ | 115 |
| 24 | IA | F | $\underset{SO_2-\triangleleft}{N\!\!-\!\!SO_2-CH_3}$ | H | $CClF_2$ | $CH_3$ | 105 |
| 25 | IB | F | $\underset{SO_2-C_2H_5}{N\!\!-\!\!SO_2-C_2H_5}$ | H | $CF_3$ | $CH_3$ | δ = 6.62 singlet 1H |
| 26 | IA | F | $\underset{SO_2-C_3H_7\text{-}n}{N\!\!-\!\!SO_2-C_2H_5}$ | H | $CF_3$ | $CH_3$ | 208 |
| 27 | IA | F | $-N(SO_2C_2H_5)_2$ | H | $CF_3$ | $C_2H_5$ | 176 |
| 28 | IB | F | $-N(SO_2C_2H_5)_2$ | H | $CF_3$ | $C_2H_5$ | 210 |
| 29 | IA | F | $\underset{SO_2-C_6H_5}{N\!\!-\!\!SO_2-CH_3}$ | H | $CF_3$ | H | 263 |
| 30 | IA | F | $\underset{SO_2-C_6H_5}{N\!\!-\!\!SO_2-CH_3}$ | H | $CF_3$ | $CH_3$ | 274 |
| 31 | IA | F | $\underset{SO_2-C_4H_9}{N\!\!-\!\!SO_2-CH_3}$ | H | $CF_3$ | H | (amorphous) |

TABLE 2-continued

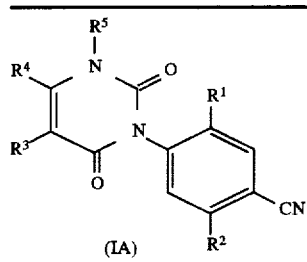

(IA)

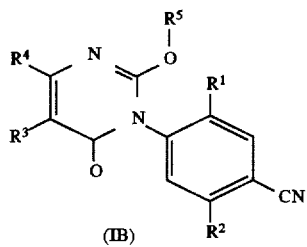

(IB)

Examples of the compounds of the formula (I)

| Ex. No. | Gen. formula | $R^1$ | $R^2$ | $R^3$ | $R^4$ | $R^5$ | Melting point (°C.) |
|---|---|---|---|---|---|---|---|
| 32 | IA | F | N(SO$_2$—CH$_3$)(SO$_2$—C$_4$H$_9$) | H | CF$_3$ | CH$_3$ | 187 |
| 33 | IA | F | N(SO$_2$—CH$_3$)(SO$_2$—CH$_2$CF$_3$) | H | CF$_3$ | H | 174 |
| 34 | IA | F | N(SO$_2$—CH$_3$)(SO$_2$—C$_2$H$_5$) | H | CF$_3$ | NH$_2$ | 113 |
| 35 | IA | F | —N(SO$_2$C$_2$H$_5$)$_2$ | H | CF$_3$ | NH$_2$ | 161 |
| 36 | IA | F | —N(SO$_2$CH$_3$)$_2$ | H | CF$_3$ | H | 193 |
| 37 | IA | F | N(SO$_2$—CH$_3$)(SO$_2$—CH(CH$_3$)$_2$) | H | CF$_3$ | CH$_3$ | 96 |
| 38 | IA | F | N(SO$_2$—CH$_3$)(SO$_2$—(CH$_2$)$_3$—Cl) | H | CF$_3$ | CH$_3$ | 212 |
| 39 | IA | H | —N(SO$_2$CH$_3$)$_2$ | H | CF$_3$ | H | 250 |
| 40 | IA | H | —N(SO$_2$CH$_3$)$_2$ | H | CF$_3$ | CH$_3$ | 284 |
| 41 | IA | F | N(SO$_2$—CH$_3$)(SO$_2$—CH$_2$—C(CH$_3$)=CH$_2$) | H | CF$_3$ | CH$_3$ | 238 |
| 42 | IA | F | N(SO$_2$—CH$_3$)(SO$_2$—CH=CH$_2$) | H | CF$_3$ | CH$_3$ | 224 |
| 43 | IB | F | —N(SO$_2$CH$_3$)$_2$ | H | CF$_3$ | CH$_3$ | 198 |
| 44 | IA | F | —N(SO$_2$CH$_3$)$_2$ | H | CF$_3$ | NH$_2$ | 279 |

The compound listed in Table 2 as Example 34 can be prepared for example as follows:

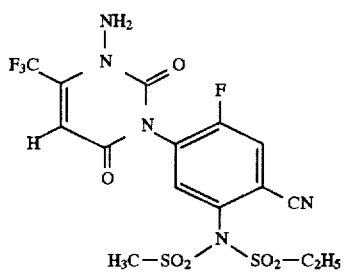

2.7 g (5.5 mmol) of 1-[4-cyano-2-fluoro-5-(N-ethylsulphonyl-N-methylsulphonylamino)-phenyl]-3,6-dihydro-2,6-dioxo-4-trifluoromethyl-1(2H)-pyrimidine are dissolved in 10 g of N,N-dimethyl-formamide, and 0.3 g of 60% sodium hydride (7.5 mmol of NaH) is added to this solution at approximately 10° C. The mixture is stirred for 15 minutes, and 1.1 g (5.5 mmol) of 1-aminooxy-2,4-dinitro-benzene is then added in small portions at approximately 10° C. The reaction mixture is stirred for 3 days at approximately 20° C. The mixture is then diluted with 100 ml of ethyl acetate and poured into approximately 800 ml of dilute aqueous sodium chloride solution. The aqueous phase is extracted three times using ethyl acetate, and the combined organic extraction solutions are washed with water, dried using sodium sulphate and filtered. The filtrate is concentrated and the residue purified by column chromatography (cyclohexane/ethyl acetate, vol. 2/1).

0.40 g (15% of theory) of 1-[4-cyano-2-fluoro-5-(N-ethylsulphonyl-N-methylsulphonylamino)-phenyl]-5-amino-3,6-dihydro-2,6-dioxo-4-trifluoromethyl-1(2H)-pyrimidine of melting point 113° C. is obtained from the main fraction.

Examples of the conversion according to the invention:

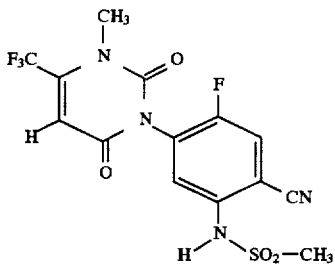

A mixture of 0.97 g (2 mmol) of 1-[4-cyano-2-fluoro-5-(bis-methylsulphonyl-amino)-phenyl]-3,6-dihydro-2,6-dioxo-3-methyl-4-trifluoromethyl-1(2H)-pyrimidine, 10 ml of water, 0.38 g (4 mmol) of sodium hydrogen carbonate and 20 ml of acetone is stirred for 2 days at 20° C. The acetone is then distilled off, and the aqueous solution is acidified with 2N hydrochloric acid and shaken with ethyl acetate. The organic phase is dried using sodium sulphate and filtered. The filtrate is concentrated, and the residue is taken up in 1 ml of ethyl acetate, diluted with diethyl ether and filtered off with suction.

0.70 g (86% of theory) of 1-(4-cyano-2-fluoro-5-methylsulphonyl-amino-phenyl)-3,6-dihydro-2,6-dioxo-3-methyl-4-trifluoromethyl-1(2H)-pyrimidine of melting point 192° C. is obtained.

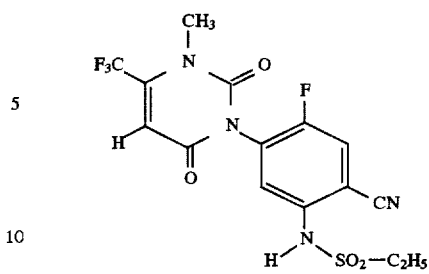

A mixture of 34 g (66 mmol) of 1-[4-cyano-2-fluoro-5-(bis-ethylsulphonyl-amino)-phenyl]-3,6-dihydro-2,6-dioxo-3-methyl-4-trifluoromethyl-1(2H)-pyrimidine, 250 ml of water, 11.1 g (130 mmol) of sodium hydrogen carbonate and 250 ml of acetone is stirred for 8 hours at 50° C. The acetone is subsequently distilled off, and the remainder of the reaction mixture is diluted with 500 ml of water and filtered. The filtrate is then acidified with 2N hydrochloric acid and filtered with suction. The crystalline product is recrystallized from diethyl ether/ethyl acetate (vol.: 95/5).

22 g ((79% of theory) of 1-(4-cyano-2-fluoro-5-ethylsulphonyl-amino-phenyl)-3,6-dihydro-2,6-dioxo-3-methyl-4-trifluoromethyl-1(2H)-pyrimidine of melting point 172° C. are obtained.

Use Examples

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, a very powerful action against weeds combined with a good tolerance by crop plants, such as, for example, wheat, is shown, for example, by the compounds of Preparation Examples 2, 4, 6, 13 and 15.

Example B

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound at the desired concentration and are infested with mustard beetle larvae *Phaedon cochleariae*, while the leaves are still moist.

37

After the specified periods of time, the destruction in % is determined. 100% means that all the beetle larvae have been killed; 0% means that none of the beetle larvae have been killed.

In this test, a powerful activity is shown, for example, by the compound of Preparation Example 3.

Example C

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound at the desired concentration and are infested with caterpillars of the diamond-back moth *Plutella maculipennis*, while the leaves are still moist.

After the specified periods of time, the destruction in % is determined. 100% means that all the caterpillars have been killed; 0% means that none of the caterpillars have been killed.

In this test, a powerful activity is shown, for example, by the compound of Preparation Example 3.

Example D

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound at the desired concentration and are infested with caterpillars of the fall armyworm *Spodoptera frugiperda*, while the leaves are still moist.

After the specified periods of time, the destruction in % is determined. 100% means that all the caterpillars have been killed; 0% means that none of the caterpillars have been killed.

In this test, a powerful activity is shown, for example, by the compound of Preparation Example 3.

We claim:

1. Process for the preparation of N-cyanoaryl nitrogen heterocycles of the general formula (I)

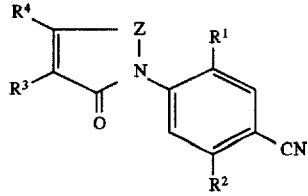

in which $R^1$ represents hydrogen, fluorine or chlorine,

38

$R^2$ represents the group below

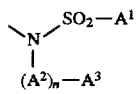

where n represents the numbers 0 or 1, $A^1$ represents methyl, ethyl, n- or i-propyl, n-, i-, s- or t-butyl, n-, i-, s- or t-pentyl, each of which is optionally substituted by fluorine or chlorine, $A^1$ furthermore represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, methyl and/or ethyl, $A^1$ furthermore represents phenyl, naphthyl, phenylmethyl or phenylethyl, each of which is optionally substituted by fluorine, chlorine, bromine, cyano, nitro, carboxyl, methyl, trifluoromethyl, methoxy, ethoxy, difluoromethoxy, trifluoromethoxy, methylthio, ethylthio, methylsulphinyl, ethylsulphinyl, methylsulphonyl, ethylsulphonyl, dimethylaminosulphonyl, methoxycarbonyl, ethoxycarbonyl, propoxycarbonyl or phenyl, $A^1$ furthermore represents thienyl, pyrazolyl or pyridyl, each of which is optionally substituted by fluorine, chlorine, bromine, cyano, methyl, ethyl, trifluoromethyl, methoxy, ethoxy, methylthio, ethylthio, methylsulphinyl, ethylsulphinyl, methylsulphonyl, ethylsulphonyl, methoxycarbonyl or ethoxycarbonyl, $A^2$ represents methylene or dimethylene, and $A^3$ represents formyl, or represents acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, each of which is optionally substituted by fluorine, chlorine, methoxy or ethoxy, or represents cyclopropylcarbonyl, cyclobutylcarbonyl, cyclopentylcarbonyl, cyclohexylcarbonyl, cyclopropylmethylcarbonyl, cyclobutylmethylcarbonyl, cyclopentylmethylcarbonyl, cyclohexylmethylcarbonyl, cyclopropylsulphonyl, cyclobutylsulphonyl, cyclopentylsulphonyl, cyclohexylsulphonyl, cyclopropylmethylsulphonyl, cyclobutylmethylsulphonyl, cyclopentylmethylsulphonyl or cyclohexylsulphonyl, each of which is optionally substituted by fluorine, chlorine, bromine, cyano, methyl or ethyl, or represents phenylcarbonyl, phenylmethylcarbonyl, phenoxycarbonyl, phenylsulphonyl, naphthylsulphonyl, phenylmethylsulphonyl, thienylsulphonyl or pyridinylsulphonyl (which are in each case optionally substituted by fluorine, chlorine, bromine, cyano, methyl, ethyl, methoxy, ethoxy, trifluoromethyl, difluoromethyl, difluoromethoxy, trifluoromethoxy, methoxycarbonyl or ethoxycarbonyl), $R^3$ represents hydrogen, fluorine, chlorine, bromine, or represents methyl, ethyl, n- or i-propyl, each of which is optionally substituted by fluorine and/or chlorine, $R^4$ represents methyl, ethyl, n- or i-propyl, each of which is optionally substituted by fluorine and/or chlorine, or together with $R^3$ represents trimethylene or tetramethylene, and Z represents one of the groups below

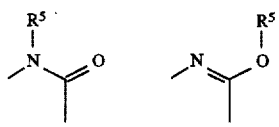

where $R^5$ represents hydrogen, or represents methyl, ethyl, n- or i-propyl, n-, i- or s-butyl, propenyl, butenyl, propinyl, butinyl, acetyl, propionyl, methoxycarbonyl or ethoxycarbonyl, each of which is optionally substituted by fluorine, chlorine or cyano, or represents amino or hydroxyl (in each case only bonded to N), wherein (a) to prepare compounds of the formula (IA) and (IB)

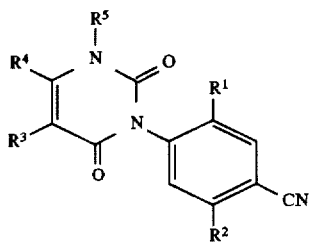

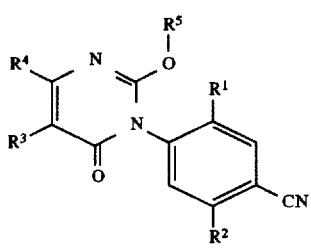

in which $R^5$ represents hydrogen and $R^1$, $R^2$, $R^3$ and $R^4$ have the abovementioned meanings, aminoalkenoic esters of the general formula (II)

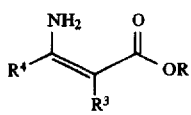

in which $R^3$ and $R^4$ have the abovementioned meanings and

R represents alkyl, aryl or arylalkyl, are reacted with cyanoaryl isocyanates of the general formula (III)

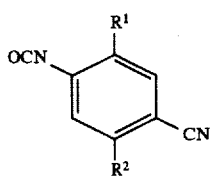

in which $R^1$ and $R^2$ have the abovementioned meanings, or with cyanoarylurethanes (cyanoarylcarbamates) of the general formula (IV)

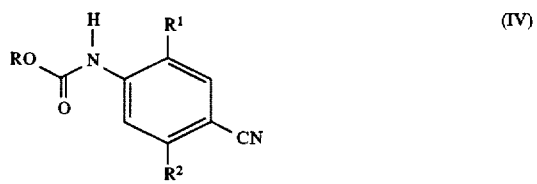

in which $R^1$ and $R^2$ have the abovementioned meanings and

R represents alkyl, aryl or arylalkyl, if appropriate in the presence of a reaction auxiliary and if appropriate in the presence of a diluent, or in that (b) to prepare compounds of the formulae (IA) and/or (IB) in which $R^5$ represents in each case optionally substituted alkyl, alkenyl, alkinyl, alkylcarbonyl or alkoxycarbonyl and $R^1$, $R^2$, $R^3$ and $R^4$ have the abovementioned meanings, N-cyanoaryl nitrogen heterocycles of the general formulae (IA) and/or (IB)

in which $R^5$ represents hydrogen and $R^1$, $R^2$, $R^3$ and $R^4$ have the abovementioned meanings, are reacted with alkylating agents or acylating agents of the general formulae (V) or (VI)

in which $R^5$ represents in each case optionally substituted alkyl, alkenyl, alkinyl, alkylcarbonyl or alkoxycarbonyl and $X^1$ in formula (V) represents halogen, if appropriate in the presence of an acid acceptor and if appropriate in the presence of a diluent, or in that (c) to prepare compounds of the formula (I) in which $R^2$ represents the following group

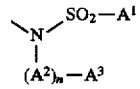

and n, $A^1$, $A^2$, $A^3$, $R^1$, $R^3$, $R^4$ and Z have the abovementioned meanings, N-cyanoaryl nitrogen heterocycles of the general formula (I) in which $R^2$ represents the group —NH—$SO_2$—$A^1$ and $A^1$, $R^1$, $R^3$, $R^4$ and Z have the abovementioned meanings, are reacted with halogen compounds of the general formula (VII)

in which n, $A^2$ and $A^3$ have the abovementioned meanings and $X^2$ represents halogen, if appropriate in the presence of an acid acceptor and if appropriate in the presence of a diluent, or in that (d) to prepare compounds of the formula (IA) in which $R^5$ represents amino or hydroxyl and $R^1$, $R^2$, $R^3$ and $R^4$ have the abovementioned meanings, N-cyanoaryl nitrogen heterocycles of the general formulae (IA) and/or (IB) in which $R^5$ represents hydrogen and $R^1$, $R^2$, $R^3$ and $R^4$ have the abovementioned meanings, are reacted with electrophilic aminating or hydroxylating agents, if appropriate in the presence of an acid acceptor and if appropriate in the presence of a diluent.

2. Process for the preparation of herbicidal and insecticidal compositions, characterized in that N-cyanoaryl nitrogen heterocycles of the formula (I) according to claim 1 are mixed with extenders and/or surface-active substances.

3. N-cyanoaryl nitrogen heterocycles of the formula

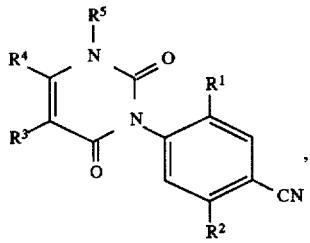

wherein the substituents are as follows:

| $R^1$ | $R^2$ | $R^3$ | $R^4$ | $R^5$ |
|---|---|---|---|---|
| F | $-N(SO_2C_2H_5)(COtC_4H_9)$ | H | $CF_3$ | $CH_3$ |
| F | $-N(SO_2C_2H_5)(COCH_3)$ | H | $CF_3$ | $CH_3$ |
| F | $-N(SO_2C_2H_5)(COC_2H_5)$ | H | $CF_3$ | $CH_3$ |
| F | $-N(SO_2C_2H_5)(COiC_3H_7)$ | H | $CF_3$ | $CH_3$ |
| F | $-N(SO_2C_2H_5)(COnC_4H_9)$ | H | $CF_3$ | $CH_3$ |
| F | $-N(SO_2C_2H_5)(COnC_3H_7)$ | H | $CF_3$ | $CH_3$ |
| F | $-N(SO_2CH_3)(COtC_4H_9)$ | H | $CF_3$ | $CH_3$ |
| F | $-N(SO_2CH_3)(COCH_3)$ | H | $CF_3$ | $CH_3$ |
| F | $-N(SO_2CH_3)(COCH_2Cl)$ | H | $CF_3$ | $CH_3$ |
| F | $-N(SO_2CH_3)(COC_2H_5)$ | H | $CF_3$ | $CH_3$ |
| F | $-N(SO_2CH_3)(COiC_3H_7)$ | H | $CF_3$ | $CH_3$ |
| F | $-N(SO_2CH_3)(COnC_3H_7)$ | H | $CF_3$ | $CH_3$ |
| F | $-N(SO_2CH_3)(COCH=CH_2)$ | H | $CF_3$ | $CH_3$ |
| F | $-N(SO_2CH_3)(COCH_2OCH_3)$ | H | $CF_3$ | $CH_3$ |
| F | $-N(SO_2C_2H_5)(COtC_4H_9)$ | H | $CF_3$ | $NH_2$ |
| F | $-N(SO_2CH_3)(COtC_4H_9)$ | H | $CF_3$ | $NH_2$ |

4. A herbicidal composition comprising a herbicidally effective amount of a compound of claim 3, and a herbicidally acceptable carrier or diluent therefor.

5. A method of combatting unwanted vegetation which comprises applying to such vegetation or to a locus from which it is desired to exclude such vegetation, a herbicidally effective amount of a compound of claim 3.

6. Ethanesulfonic acid [2-cyano-4-fluoro-5-(3-methyl-2,6-dioxo-4-trifluoromethyl-3,6-dihydro-2H-pyrimidin-1-yl)-phenyl]-(2,2-dimethyl-propionyl)-amide

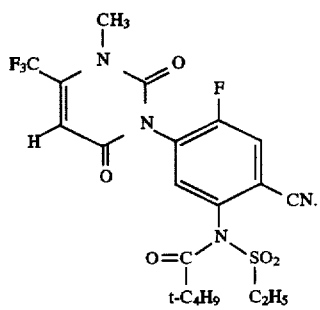

7. Ethanesulfonic acid [2-cyano-4-fluoro-5-(3-methyl-2,6-dioxo-4-trifluoromethyl-3,6-dihydro-2H-pyrimidin-1-yl)-phenyl]-acetyl-amide

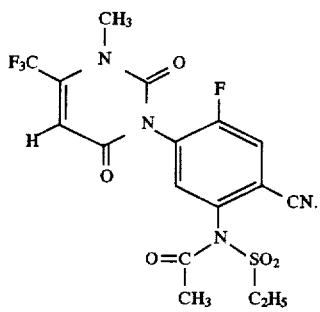

8. Ethanesulfonic acid [2-cyano-4-fluoro-5-(3-methyl-2,6-dioxo-4-trifluoromethyl-3,6-dihydro-2H-pyrimidin-1-yl)-phenyl]-n-propionyl-amide

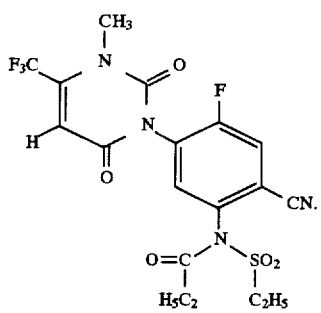

9. Ethanesulfonic acid [2-cyano-4-fluoro-5-(3-methyl-2,6-dioxo-4-trifluoromethyl-3,6-dihydro-2H-pyrimidin-1-yl-phenyl]-(2-methyl-propionyl)-amide

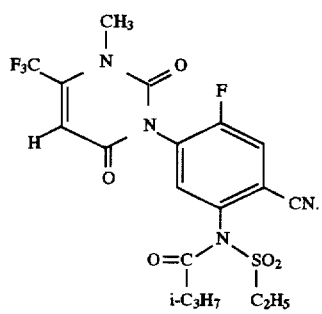

10. Ethanesulfonic acid [2-cyano-4-fluoro-5-(3-methyl-2,6-dioxo-4-trifluoromethyl-3,6-dihydro-2H-pyrimidin-1-yl)-phenyl]-n-valyryl-amide

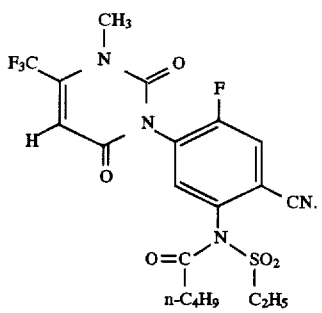

11. Ethanesulfonic acid [2-cyano-4-fluoro-5-(3-methyl-2,6-dioxo-4-trifluoromethyl-3,6-dihydro-2H-pyrimidin-1-yl)-phenyl]-n-butyryl-amide

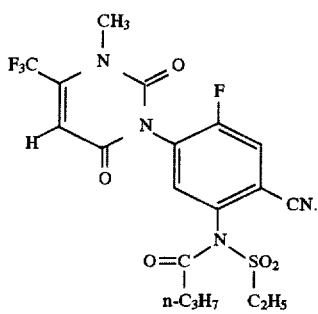

12. Methanesulfonic acid [2-cyano-4-fluoro-5-(3-methyl-2,6-dioxo-4-trifluoromethyl-3,6-dihydro-2H-pyrimidin-1-yl)-phenyl]-(2,2-dimethyl-propionyl)-amide

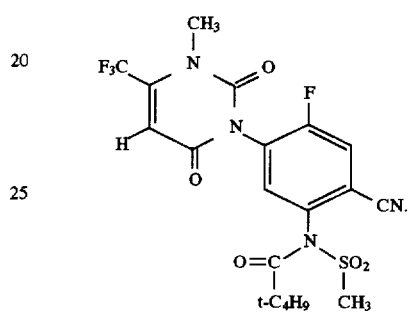

13. Methanesulfonic acid [2-cyano-4-fluoro-5-(3-methyl-2,6-dioxo-4-trifluoromethyl-3,6-dihydro-2H-pyrimidin-1-yl)-phenyl]-acetyl-amide

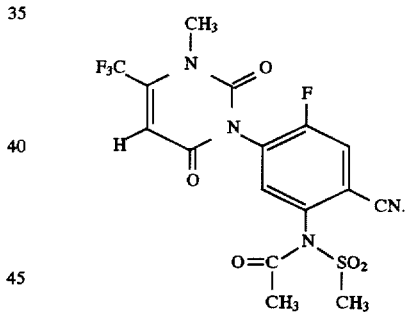

14. Methanesulfonic acid [2-cyano-4-fluoro-5-(3-methyl-2,6-dioxo-4-trifluoromethyl-3,6-dihydro-2H-pyrimidin-1-yl)-phenyl]-chloroacetyl-amide

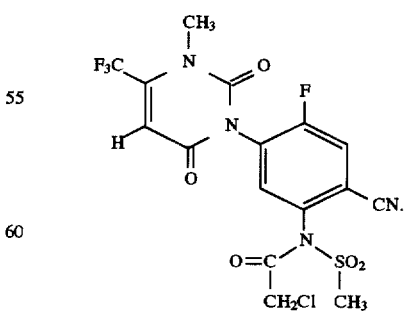

15. Methanesulfonic acid [2-cyano-4-fluoro-5-(3-methyl-2,6-dioxo-4-trifluoromethyl-3,6-dihydro-2H-pyrimidin-1-yl)-phenyl]-propionyl-amide

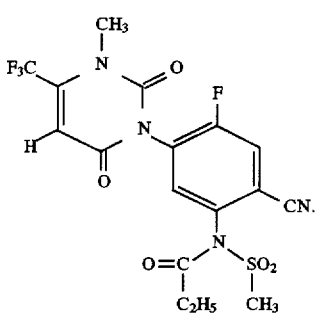

16. Methanesulfonic acid [2-cyano-4-fluoro-5-(3-methyl-2,6-dioxo-4-trifluoromethyl-3,6-dihydro-2H-pyrimidin-1-yl-phenyl]-(2-methyl-propionyl)-amide

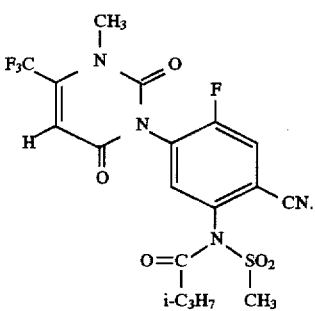

17. Methanesulfonic acid [2-cyano-4-fluoro-5-(3-methyl-2,6-dioxo-4-trifluoromethyl-3,6-dihydro-2H-pyrimidin-1-yl)-phenyl]-n-butyryl-amide

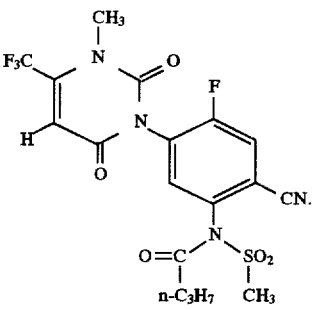

18. Methanesulfonic acid [2-cyano-4-fluoro-5-(3-methyl-2,6-dioxo-4-trifluoromethyl-3,6-dihydro-2H-pyrimidin-1-yl)-phenyl]-acryloyl-amide

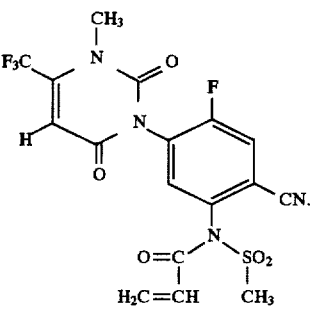

19. Methanesulfonic acid [2-cyano-4-fluoro-5-(3-methyl-2,6-dioxo-4-trifluoromethyl-3,6-dihydro-2H-pyrimidin-1-yl)-phenyl]-methoxyacetyl-amide

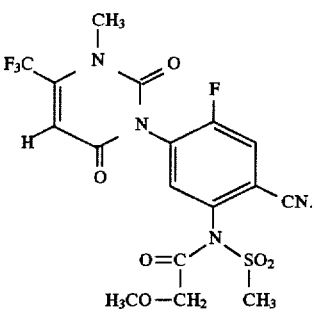

20. Ethanesulfonic acid [2-cyano-4-fluoro-5-(3-amino-2,6-dioxo-4-trifluoromethyl-3,6-dihydro-2H-pyrimidin-1-yl)-phenyl]-(2,2-dimethyl-propionyl)-amide

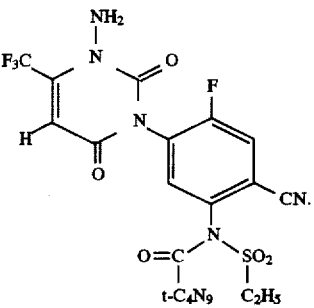

21. Methanesulfonic acid [2-cyano-4-fluoro-5-(3-amino-2,6-dioxo-4-trifluoromethyl-3,6-dihydro-2H-pyrimidin-1-yl)-phenyl]-(2,2-dimethyl-propionyl)-amide

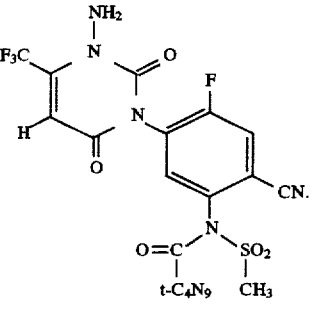

22. A method for combatting insects which comprises applying to said insects or to a habitat thereof an insecticidally effective amount of a compound of claim 3.

23. An insecticidal composition comprising an insecticidally effective amount of a compound of claim 3 and an insecticidally acceptable diluent or carrier therefor.

* * * * *

UNITED STATES PATENT AND TRADEMARK OFFICE
CERTIFICATE OF CORRECTION

PATENT NO. : 5,759,957  Page 1 of 5
DATED : June 2, 1998
INVENTOR(S) : Andree, et al.

It is certified that error appears in the above-indentified patent and that said Letters Patent is hereby corrected as shown below:

Title Page [22] Filed: Delete " Jul. 8, 1996 " and substitute -- Dec. 26, 1995 --

Title Page Insert -- [62] Related U.S. Application Data: Continuation-in-part of application serial no. PCT/EP95/01351 filed on April 12, 1995 in Europe --

Col. 33-34, 3rd line from bottom  After and below " Ex. No. 44 " Insert

| | | | | | | | |
|---|---|---|---|---|---|---|---|
| -- 45 | IA | F | -N(SO$_2$C$_2$H$_5$)(COtC$_4$H$_9$) | H | CF$_3$ | CH$_3$ | 175 |
| 46 | IA | F | -N(SO$_2$C$_2$H$_5$)(COCH$_3$) | H | CF$_3$ | CH$_3$ | 213 |
| 47 | IA | F | -N(SO$_2$C$_2$H$_5$)(COC$_2$H$_5$) | H | CF$_3$ | CH$_3$ | 208 |
| 48 | IA | F | -N(SO$_2$C$_2$H$_5$)(COiC$_3$H$_7$) | H | CF$_3$ | CH$_3$ | 199 -- |

UNITED STATES PATENT AND TRADEMARK OFFICE
CERTIFICATE OF CORRECTION

PATENT NO. : 5,759,957
DATED : June 2, 1998
INVENTOR(S) : Andree, et al.

It is certified that error appears in the above-identified patent and that said Letters Patent is hereby corrected as shown below:

Col. 33-34, 3rd line from bottom Cont'd

| Ex. No. | Gen. formula | $R^1$ | $R^2$ | $R^3$ | $R^4$ | $R^5$ | Melting point (°C) |
|---|---|---|---|---|---|---|---|
| 49 | IA | F | $-N\diagup^{SO_2C_2H_5}_{\diagdown COnC_4H_9}$ | H | $CF_3$ | $CH_3$ | 152 |
| 50 | IA | F | $-N\diagup^{SO_2C_2H_5}_{\diagdown COnC_3H_7}$ | H | $CF_3$ | $CH_3$ | 126 |
| 51 | IA | F | $-N\diagup^{SO_2CH_3}_{\diagdown COtC_4H_9}$ | H | $CF_3$ | $CH_3$ | 218 |
| 52 | IA | F | $-N\diagup^{SO_2CH_3}_{\diagdown COCH_3}$ | H | $CF_3$ | $CH_3$ | 201 |

UNITED STATES PATENT AND TRADEMARK OFFICE
CERTIFICATE OF CORRECTION

PATENT NO. : 5,759,957
DATED : June 2, 1998
INVENTOR(S) : Andree, et al.

It is certified that error appears in the above-indentified patent and that said Letters Patent is hereby corrected as shown below:

Col. 33-34, 3rd line from bottom Cont'd

| Ex. No. | Gen. formula | $R^1$ | $R^2$ | $R^3$ | $R^4$ | $R^5$ | Melting point (°C) |
|---|---|---|---|---|---|---|---|
| 53 | IA | F | $-N\begin{smallmatrix}SO_2CH_3\\COCH_2Cl\end{smallmatrix}$ | H | $CF_3$ | $CH_3$ | 92 |
| 54 | IA | F | $-N\begin{smallmatrix}SO_2CH_3\\COC_2H_5\end{smallmatrix}$ | H | $CF_3$ | $CH_3$ | 193 |
| 55 | IA | F | $-N\begin{smallmatrix}SO_2CH_3\\COiC_3H_7\end{smallmatrix}$ | H | $CF_3$ | $CH_3$ | 208 |
| 56 | IA | F | $-N\begin{smallmatrix}SO_2CH_3\\COnC_3H_7\end{smallmatrix}$ | H | $CF_3$ | $CH_3$ | 172 |

UNITED STATES PATENT AND TRADEMARK OFFICE
CERTIFICATE OF CORRECTION

PATENT NO. : 5,759,957
DATED : June 2, 1998
INVENTOR(S) : Andree, et al.

Page 4 of 5

It is certified that error appears in the above-indentified patent and that said Letters Patent is hereby corrected as shown below:

Col. 33-34, 3rd line from bottom Cont'd

| Ex. No. | Gen. for-mula | $R^1$ | $R^2$ | $R^3$ | $R^4$ | $R^5$ | Melting point (°C) |
|---|---|---|---|---|---|---|---|
| 57 | IA | F | $-N\begin{matrix}SO_2CH_3\\COCH=CH_2\end{matrix}$ | H | $CF_3$ | $CH_3$ | 202 |
| 58 | IA | F | $-N\begin{matrix}SO_2CH_3\\COCH_2OCH_3\end{matrix}$ | H | $CF_3$ | $CH_3$ | 169 |
| 59 | IA | F | $-N\begin{matrix}SO_2C_2H_5\\COtC_4H_9\end{matrix}$ | H | $CF_3$ | $NH_2$ | 199 |
|  |  |  |  |  |  |  | -- |

UNITED STATES PATENT AND TRADEMARK OFFICE
CERTIFICATE OF CORRECTION

PATENT NO. : 5,759,957
DATED : June 2, 1998
INVENTOR(S) : Andree, et al.

It is certified that error appears in the above-indentified patent and that said Letters Patent is hereby corrected as shown below:

Col. 33-34, 3rd line from bottom Cont'd

| Ex. No. | Gen. formula | $R^1$ | $R^2$ | $R^3$ | $R^4$ | $R^5$ | Melting point (°C) |
|---|---|---|---|---|---|---|---|
| 60 | IA | F |  | H | $CF_3$ | $NH_2$ | 213 destr. |

Signed and Sealed this

Second Day of March, 1999

Q. TODD DICKINSON

Acting Commissioner of Patents and Trademarks